(12) United States Patent
Cao

(10) Patent No.: US 8,008,074 B2
(45) Date of Patent: Aug. 30, 2011

(54) COMPOSITIONS AND METHODS FOR IMPROVING BONE MASS THROUGH MODULATION OF RECEPTORS OF PTH AND FRAGMENTS THEREOF

(75) Inventor: Xu Cao, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 197 days.

(21) Appl. No.: 12/293,713

(22) PCT Filed: Mar. 20, 2007

(86) PCT No.: PCT/US2007/064408
§ 371 (c)(1),
(2), (4) Date: Sep. 19, 2008

(87) PCT Pub. No.: WO2007/109668
PCT Pub. Date: Sep. 27, 2007

(65) Prior Publication Data
US 2010/0160220 A1    Jun. 24, 2010

Related U.S. Application Data

(60) Provisional application No. 60/743,567, filed on Mar. 20, 2006.

(51) Int. Cl.
*C12N 5/00* (2006.01)
*A61K 38/00* (2006.01)
*A61K 38/18* (2006.01)
*A61K 38/29* (2006.01)
*C07K 14/00* (2006.01)

(52) U.S. Cl. ......... 435/375; 514/8.8; 514/8.9; 514/11.8; 514/16.7; 435/7.1; 530/350

(58) Field of Classification Search ................ None
See application file for complete search history.

(56) References Cited

OTHER PUBLICATIONS

Martin et al., 2006, "Mechanisms Involved in Skeletal Anabolic Therapies," Ann. N.Y. Acad. Sci. vol. 1068, pp. 458-470.
PCT International Search Report for PCT/US07/64408 dated Aug. 21, 2008 (2 pages).
Atfi et al., 2010, "PTH Battles TGF-beta in Bone," Nature Cell Biology, vol. 12(3):205-207.
Iqbal et al., 2009, "Coupling Bone Degradation to Formation," Nature Medicine, vol. 15(7):729-731.
Qiu et al., 2010, "TGF-beta Type II Receptor Phosphorylates PTH Receptor to Integrate Bone Remodelling Signalling," Nature Cell Biology, vol. 12(3):224-234 with Supplementary Information.
Tang et al., 2009, "TGF-beta1-Induced Migration of Bone Mesenchymal Stem Cells Couples Bone Resorption with Formation," Nature Medicine, vol. 15(7):757-765.

*Primary Examiner* — Bridget E Bunner
*Assistant Examiner* — Xiaozhen Xie
(74) *Attorney, Agent, or Firm* — McKeon Meunier Carlin & Curfman LLC

(57) ABSTRACT

The present invention relates to the discovery of novel receptors for the signaling of PTH and/or fragments of PTH, and the role of cPTH in bone development. The novel PTH receptors identified are selected from the group consisting of LRP5/6, TGFβRII, BMPRII (long form and short form), ActRIIA, and ActRIIB. Specifically, the present invention provides a novel screening tool for identifying compounds that improve bone mass by affecting certain pathways that promote or downregulate bone-forming activity. This promotion of bone-forming activity could provide for treatments for bone-loss or bone density disorders and/or kidney disease. The invention further encompasses the compounds, PTH ligands, and fragments of PTH ligands described herein; pharmaceutical compositions comprising the compounds, PTH ligands, or fragments of PTH ligand; and methods of increasing bone density using the compounds, PTH ligands, or fragments of PTH ligands.

8 Claims, 22 Drawing Sheets a b c a b c a b c a b c d

A

B a b

A

B

C

1 ---
2 Act-RIIA
3 Act-RIIB
4 Bam-Bi
5 PTH-R

A

B

COMPOSITIONS AND METHODS FOR IMPROVING BONE MASS THROUGH MODULATION OF RECEPTORS OF PTH AND FRAGMENTS THEREOF

CROSS REFERENCE TO RELATED APPLICATIONS

This application claims the priority benefit of PCT/US2007/064408 filed on Mar. 20, 2007 and U.S. Provisional Application No. 60/743,567, filed Mar. 20, 2006, the contents of which are hereby incorporated in their entireties by this reference.

ACKNOWLEDGMENT OF FEDERAL RESEARCH SUPPORT

This invention was made, at least in part, with funding from the National Institutes of Health (Award Number R01DK57501). Accordingly, the United States Government has certain rights in this invention.

FIELD OF THE INVENTION

The present invention relates to the discovery of novel receptors that bind to and confer activity to PTH ligands and fragments of PTH ligands, including carboxy-terminal fragments of PTH (cPTH). Specifically, the present invention envisions a novel screening tool for the determination of compounds, PTH polypeptides, and/or fragments of PTH polypeptides capable of modulating the activity of classical PTH receptors and/or novel receptors for PTH and/or fragments of PTH, including cPTH, and that could be used in the treatment of various bone-loss or other bone disorders.

BACKGROUND

Bone loss and osteoporosis are major public health problems in the elderly. With people in the United States living longer than before, the number of people that will develop age-related bone loss and osteoporosis is expected to rise drastically in the coming decades. Osteoporosis not only presents problems in and of itself, but with joint replacement and musculoskeletal disorders requiring manipulation and repair of bone or boney tissue, depleted bone mass presents additional problems to an aging population.

Bone is comprised of several different cell types. Osteoblasts lay down new bone from the minerals present in the extracellular milieu around the cells. Osteoclasts remove old bone, releasing the minerals compiled within bone back into the extracellular matrix. This balance between adequate new bone being deposited and old bone being removed is what gives bone its extremely beneficial properties. Osteoblasts originate from mesenchymal stem cells while osteoclasts originate from hematopoietic stem cells.

Osteoblast differentiation is a crucial aspect of bone formation and remodeling. Osteoporosis is one disorder that reflects a flaw in this delicate balance. The process of new bone formation involves the recruitment of osteoprogenitor cells that, with the appropriate stimulation, undergo proliferation and differentiate into preosteoblasts and then into mature osteoblasts to synthesize inorganic matrix into mineralized bone.

Parathyroid hormone (PTH) is a major systemic regulator of the concentrations of calcium, phosphate, and active vitamin D metabolites in blood and of cellular activity in bone. PTH is the only anabolic agent clinically used to treat osteoporosis (Rosen, 2004, Trends Endocrinol. Metab. 15:229-233). Intermittent PTH treatment can lead to an increase in bone mass and strength with a corresponding decrease in fracture risk, whereas continuous PTH impairs bone quality and can result in bone pain and pathological fractures (for review, see Murray et al., 2006, Endocrine Reviews, 26(1):78-113). The cellular and molecular mechanisms that mediate the remarkably different effects of intermittent and continuous PTH are important but incompletely understood. In addition, PTH is a major regulator for kidney function and has been implicated in chronic kidney disease.

The amino-terminal region of PTH is known to be both necessary and sufficient for full activity at PTH/PTHrP receptors (PTH1Rs), which mediate the classical biological actions of the hormone. Additionally, it is well known that multiple carboxyl-terminal fragments of PTH (cPTH fragments) are present in blood, where they comprise the major form(s) of circulating hormone. These cPTH fragments have long been regarded as inert by-products of PTH metabolism since they neither bind to nor activate PTH1Rs. Certain observations extending over the past 20 years point to the existence of novel large carboxyl-terminal PTH fragments in blood and to receptors for these fragments that appear to mediate unique biological actions in bone and other tissues (Murray et al., 2006, Endocrine Reviews, 26(1):78-113; Divieti et al., 2005, Endocrinology, 146(4):1863-1870). While Divieti demonstrated that certain domains within cPTH are necessary for binding to a putative cPTH receptor, they have not identified or characterized any such receptor (Divieti et al., (2005) Endocrinology, 146(4):1863-1870).

The identification of novel receptors for PTH and PTH fragments provides a novel therapeutic target for the treatment of bone-related diseases and kidney disease.

SUMMARY OF THE INVENTION

The present invention provides methods of identifying a compound, PTH ligand, or fragment of PTH ligand that improve bone mass, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether an increase in interaction between the PTH receptor and PTH1R occurs in the cell contacted with the compound, PTH ligand, or fragment of PTH ligand, said increase being an indication that the compound, PTH ligand, or fragment of PTH ligand improves bone mass. In certain embodiments, the test compound, PTH ligand, or fragment of PTH ligand increases Wnt signaling by recruiting LRP5/6, increases β-catenin levels, increases LRP5/6-induced transcription, increases phosphorylation of LRP5/6, and/or increases interaction of min with LRP5/6. In other embodiments, the test compound, PTH ligand, or fragment of PTH ligand induces PTH1R internalization by recruiting TGFβRII and/or decreases TGFβ-induced transcription. The invention also provides that in certain embodiments, the test compound, PTH ligand, or fragment of PTH ligand increases PKA activity. In one embodiment, the BMPRII is either the BMPRII short form or BMPRII long form.

The present invention provides methods of identifying a compound, PTH ligand, or fragment of PTH ligand that improves bone mass, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether a decrease in translocation of a SMAD occurs in the cell contacted with the compound, PTH ligand, or fragment of PTH ligand, said decrease being an indication that the compound, PTH ligand, or fragment of PTH ligand improves bone mass. In certain embodiments, the test compound, PTH ligand, or fragment of PTH ligand decreases TGFβ-induced transcription. In one embodiment, the BMPRII is either the BMPRII short form or BMPRII long form.

The present invention provides methods of identifying a compound, PTH ligand, or fragment of PTH ligand that enhances the interaction of PTH1R with a PTH receptor, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether interaction of PTH1R with the PTH receptor is increased in the presence of the test compound, PTH ligand, or fragment of PTH ligand, an increase in said interaction being an indication that the test compound, PTH ligand, or fragment of PTH ligand enhances the interaction of PTH1R with the PTH receptor. In certain embodiments, the test compound, PTH ligand, or fragment of PTH ligand increases Wnt signaling by recruiting LRP5/6, increases β-catenin levels, increases LRP5/6-induced transcription, increases phosphorylation of LRP5/6, and/or increases interaction of axin with LRP5/6. In other embodiments, the test compound, PTH ligand, or fragment of PTH ligand induces PTH1R internalization by recruiting TGFβRII and/or decreases TGFβ-induced transcription. The invention also provides that in certain embodiments, the test compound, PTH ligand, or fragment of PTH ligand increases PKA activity. In one embodiment, the BMPRII is either the BMPRII short form or BMPRII long form.

The present invention provides methods of identifying a compound, PTH ligand, or fragment of PTH ligand that modulates interaction of cPTH and a PTH receptor, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether the interaction between one or more of the PTH receptors and cPTH is modulated in the cell contacted with the compound, PTH ligand, or fragment of PTH ligand. In certain embodiments, said modulation is an increase in interaction between cPTH and the PTH receptor. In other embodiments, said modulation is a decrease in interaction between cPTH and the PTH receptor. In certain embodiments, said modulation is an indication that the test compound, PTH ligand, or fragment of PTH ligand is capable of improving bone mass.

The present invention provides processes for making a compound, PTH ligand, or fragment of PTH ligand that improves bone mass, comprising the steps of carrying out one of the methods described herein to identify a compound, PTH ligand, or fragment of PTH ligand that improves bone mass, and manufacturing the compound, PTH ligand, or fragment of PTH ligand. The present invention provides a compound, PTH ligand, or fragment of PTH ligand identified by the methods described herein, for use in a medicament for improving bone mass.

The present invention also provides methods of improving bone mass in an individual in need thereof, comprising administering to the individual a therapeutically effective amount of a compound, PTH ligand, or fragment of PTH ligand that increases interaction between PTH1R and a PTH receptor selected from the group consisting of LRP5/6, TGFβRII, BMPRII, ActRII, and ActRIIB in a bone precursor cell.

The present invention provides methods of improving bone mass in an individual in need thereof, comprising administering to the individual a therapeutically effective amount of a compound, PTH ligand, or fragment of PTH ligand that modulates interaction of cPTH and a PTH receptor selected from the group consisting of LRP5/6, TGFβRII, BMPRII, ActRII, and ActRIIB. In certain embodiments, the compound, PTH ligand, or fragment of PTH ligand decreases the interaction of cPTH with the PTH receptor. In other embodiments, the compound, PTH ligand, or fragment of PTH ligand increases the interaction of cPTH with the PTH receptor. The invention provides that in some embodiments of these methods, the individual has a bone-related disorder selected from the group consisting of osteoporosis, rheumatoid arthritis, cancer-induced bone lesions, T-cell or B-cell malignancies, or other cancers or bone disorders.

The present invention further provides methods of identifying a compound, PTH ligand, or fragment of PTH ligand that modulates interaction of PTH1R and a PTH receptor, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether the interaction between one or more of the PTH receptors and PTH1R is modulated in the cell contacted with the compound, PTH ligand, or fragment of PTH ligand. Also provided is a compound, PTH ligand, or fragment of PTH ligand identified by this method, for use in a medicament for the treatment of chronic kidney disease.

Figure 3:
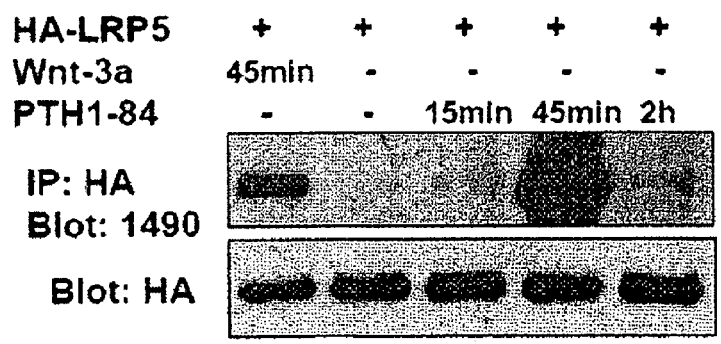
Figure 3:
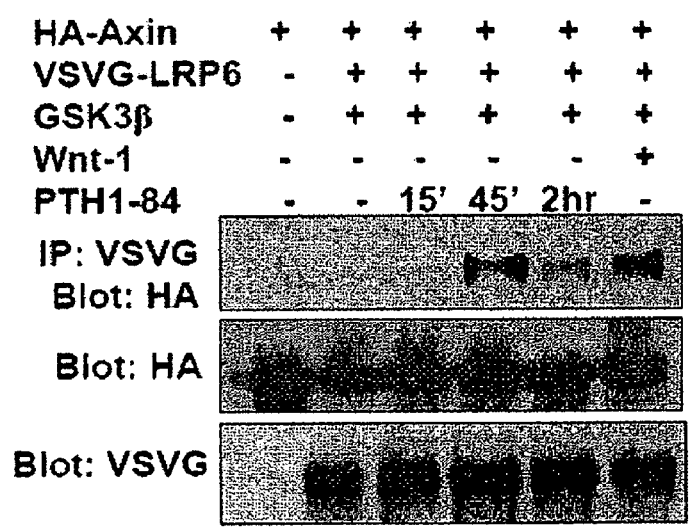
Figure 3:
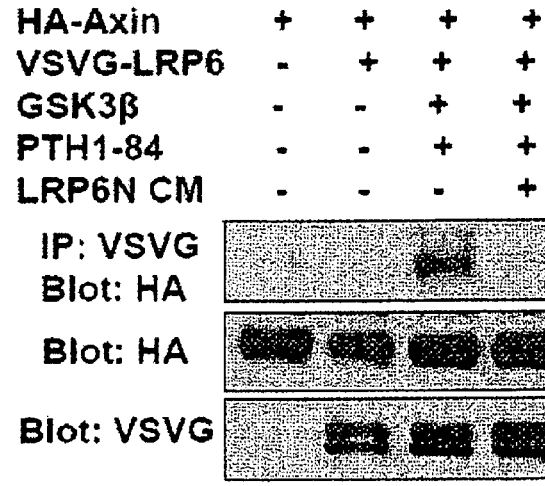
Figure 3:
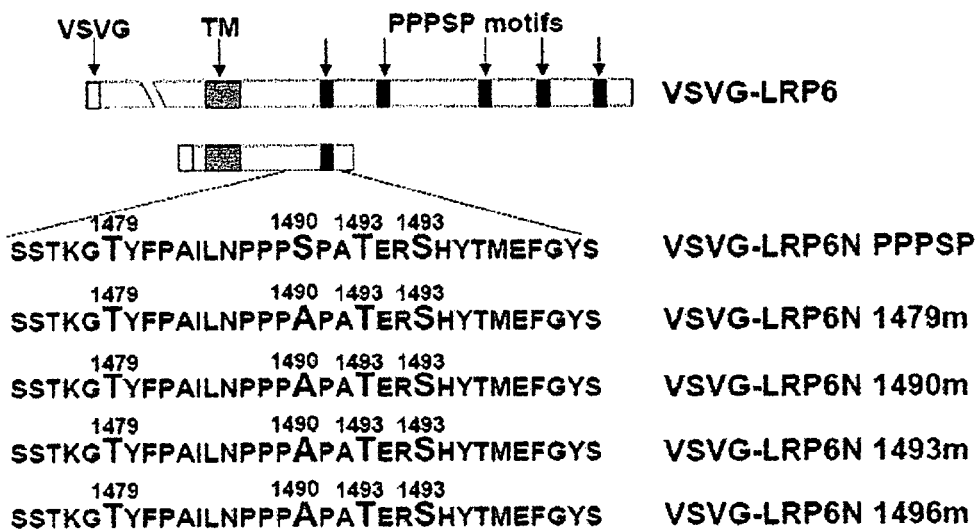
Figure 3:
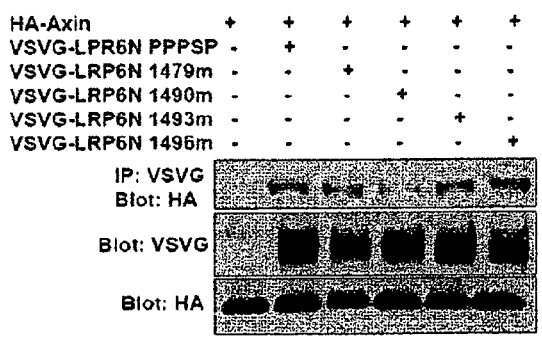
Figure 3:
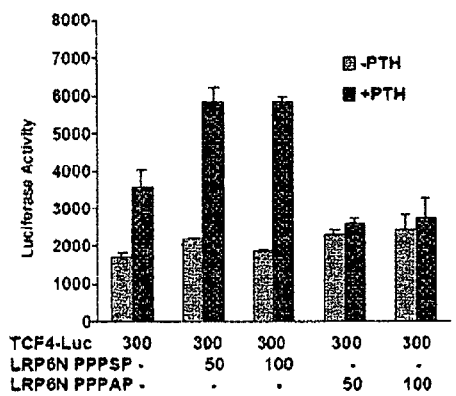

FIG. 3 shows that PTH induces LRP6 phosphorylation and LRP6/Axin binding. Panel A shows that PTH induces LRP5 PPPSP phosphorylation. HEK293 cells transfected with HA-tagged LRP5 were treated with conditioned medium containing Wnt-3a (lane 1), control medium with $5 \times 10^{-7}$ M PTH (1-84) for the indicated time periods (lane 3-5), or without PTH treatment (lane 2). Phosphorylated LRP5 was detected by Western blotting of the anti-HA immunoprecipitates with Ab1490, which specifically recognizes phosphorylated PPPSP sites within LRP5/6. Panel B shows that PTH induces LRP6/Axin binding. VSVG-tagged LRP6 was cotransfected into HEK 293 cells with HA-Axin and GSK3β, and the cells were treated with or without $10^{-7}$ M PTH (1-84) for the indicated time periods. The LRP6-associated Axin was determined by Western blotting of the anti-VSVG immunoprecipitates with anti-HA antibody. Panel C shows that LRP6N inhibits PTH-induced LRP6/Axin binding. VSVG-tagged LRP6 was cotransfected into HEK 293 cells with HA-Axin and GSK3β, and the cells were pretreated with control CM or LRP6N CM for 30 minutes, followed by treatment with or without $5 \times 10^{-7}$ M PTH (1-84) for 1 hour. The LRP6-associated Axin was determined by Western blotting of the anti-VSVG immunoprecipitates with anti-HA antibody. Panel D is a schematic of the VSVG-LRP6 wild type and mutant constructs used. Panel E shows that PPPSP is required for LRP6/Axin binding. VSVG-tagged LRP6N PPPSP or a VSVG-tagged serine/threonine mutation construct was cotransfected into HEK 293 cells with HA-Axin and GSK3β, and the cells were treated with or without $5 \times 10^{-7}$ M PTH (1-84) for 1 hour. The association of axin with wild type and mutant proteins was determined by Western blotting of the anti-VSVG immunoprecipitates with anti-HA antibody. Panel F shows that PPPSP mediates PTH-induced TCF4 activation. VSVG-tagged LRP6N PPPSP or LRP6N PPPAP was co-transfected with a TCF4-Luc plasmid in UMR 106 cells, and $5 \times 10^{-7}$ M PTH (1-84) was added for 12 hours. Then luciferase activities were determined.

Figure 4:
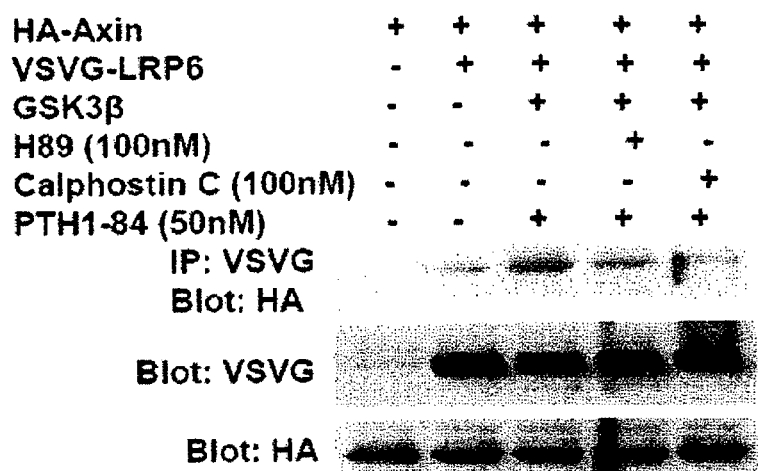
Figure 4:
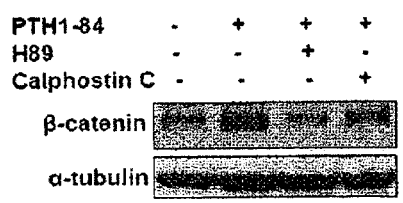
Figure 4:
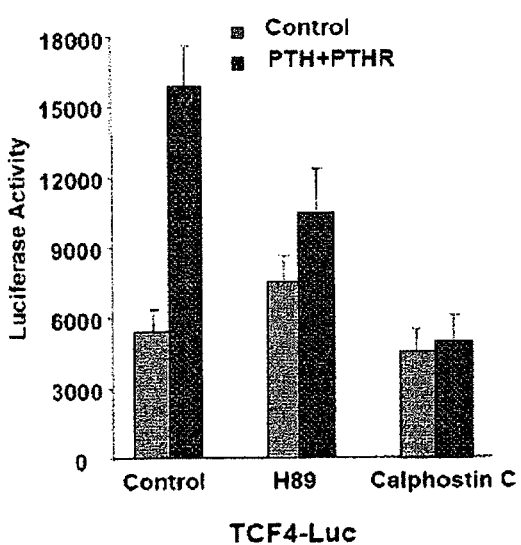

FIG. 4A shows that PKA and PKC inhibitors inhibit the binding of Axin with LRP6. VSVG-tagged LRP6 was cotransfected into HEK 293 cells with HA-Axin and GSK3β, and the cells were pre-treated with H89 or Calphostin C for 30 minutes before adding $10^{-7}$ M PTH (1-84) for another 1 hour. The LRP6-associated Axin was determined by Western blotting of the anti-VSVG immunoprecipitates. FIG. 4B shows that PKA and PKC inhibitors inhibit PTH-induced β-catenin stabilization. UMR 106 cells were treated with H89 or Calphostin C for 30 minutes before adding $10^{-7}$ M PTH (1-84) for another 1 hour. Cytosolic fractions were, prepared and analyzed by Western blotting with specific antibodies against β-catenin and α-tubulin. FIG. 4C shows that H89 and calphostin C inhibited activity from a TCF4-luciferase reporter.

Figure 5:
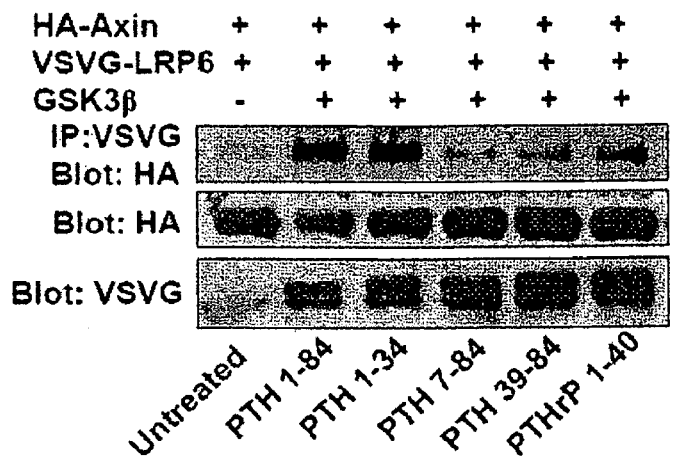
Figure 5:
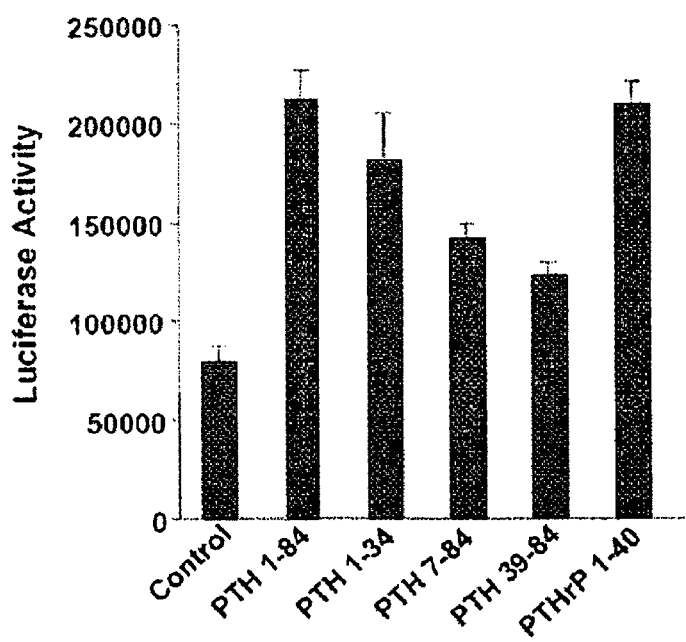
Figure 5:
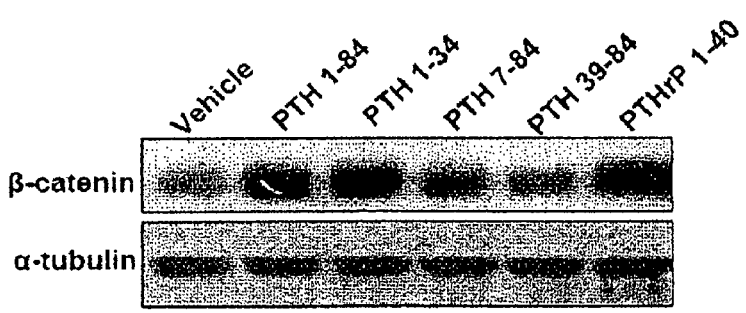

FIG. 5A shows that PTH C-terminal ligands induce minimal LRP6/Axin binding. HA-tagged LRP6 was cotransfected with HA-tagged Axin and/or GSK3β into HEK 293 cells, and the cells were treated with indicated PTH ligands for 1 hour. The LRP6-associated Axin was determined by Western blotting of the anti-VSVG immunoprecipitates. FIG. 5B is a graph showing that PTH C-terminal ligands are not able to stimulate TCF4 activity to the same extent as PTH ligand or the N-terminal fragments of PTH. UMR 106 cells were transfected with TCF4-Luc plasmid and treated with $5 \times 10^{-7}$ M of indicated PTH ligands for 12 hours. Luciferase activities were determined. FIG. 5C shows that PTH C-terminal ligands are not able to stabilize β-catenin. UMR 106 cells were treated with indicated PTH ligands for 1 hour. Cytosolic fractions were prepared and analyzed by Western blotting with specific antibodies against β-catenin and α-tubulin.

Figure 6:
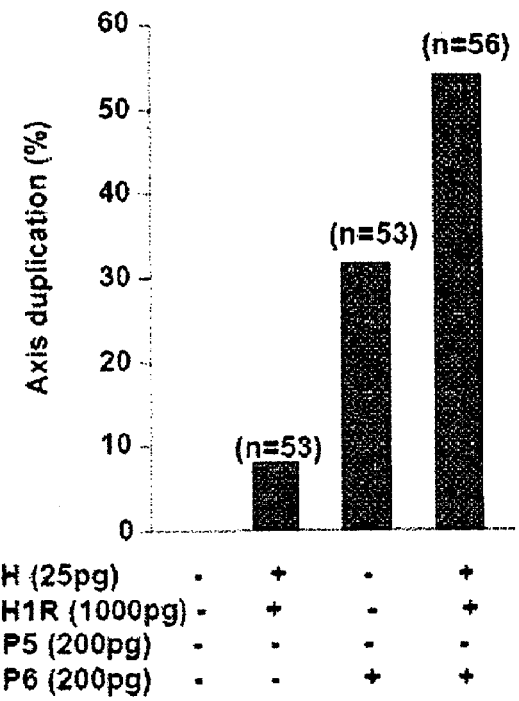

FIG. 6 shows that PTH/PTHR enhances LRP5/6-mediated axis duplication in *xenopus*. Ventral co-injection of PTH and PTH1R enhances axis duplication induced by LRP6 in *Xenopus*.

Figure 7:
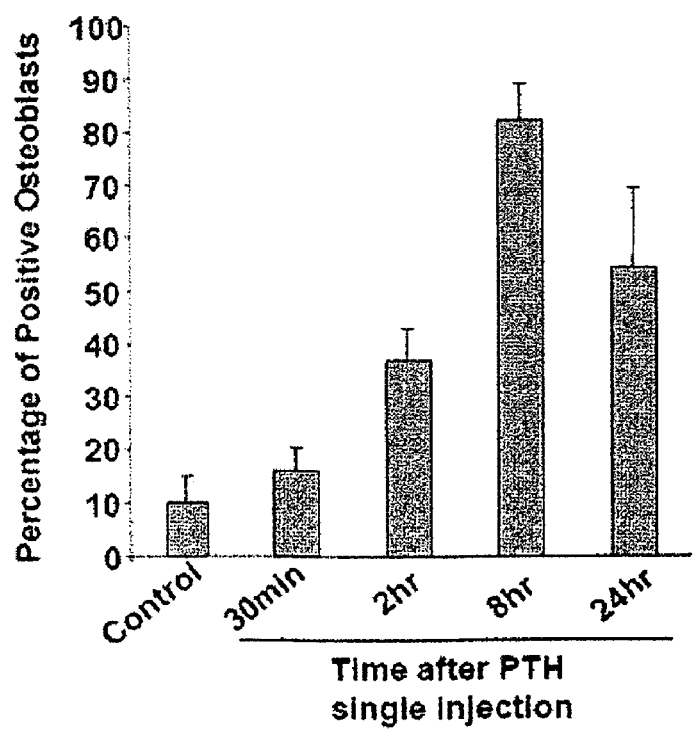
Figure 7:
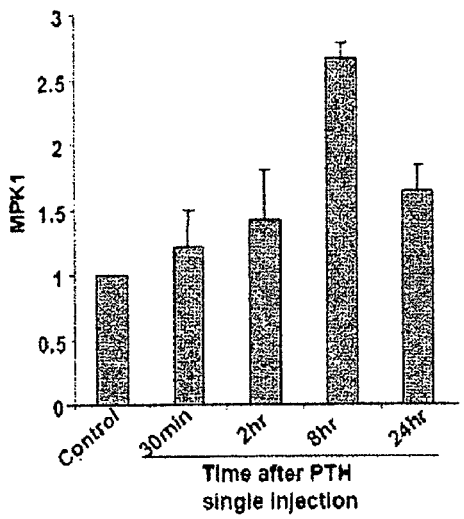
Figure 7:
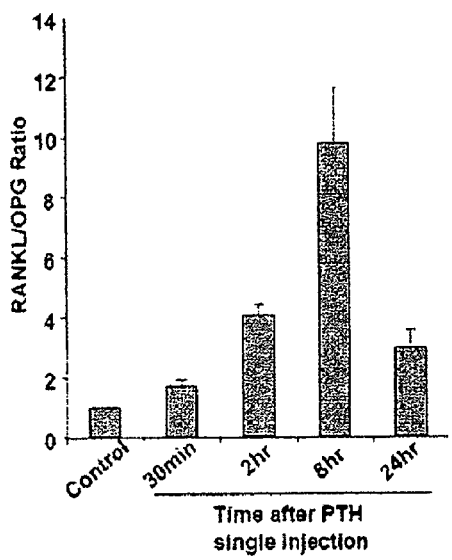
Figure 7:
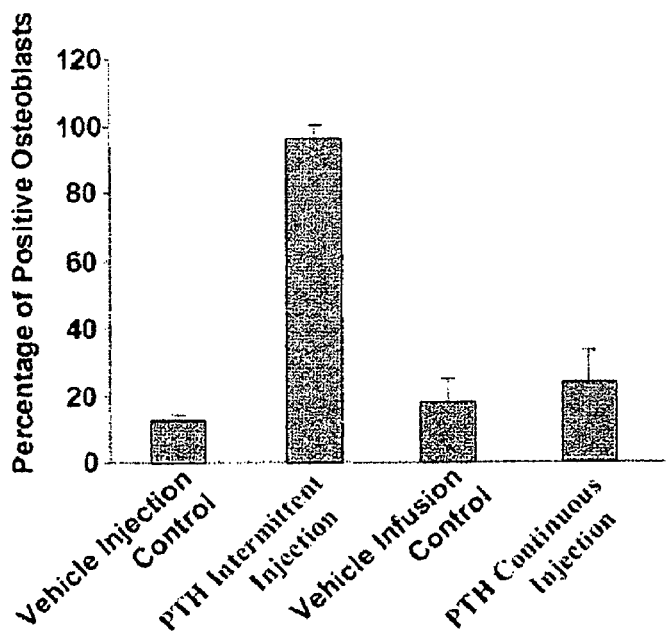

FIG. 7 shows that intermittent PTH injection elevates β-catenin protein levels exclusively in osteoblasts from mice and rat bone tissue. Immunohistochemical staining of representative sections with antibody against β-catenin at 10× objective and 40× objective counterstained with hematoxylin from either primary spongliosa subjacent to the epiphyseal growth plates or Spongiosa subjacent to diaphyseal hematopoietic bone marrow of different time points after PTH single injection in rats. Panel A shows the numbers of β-catenin-positive osteoblasts as a percent of total osteoblasts per field that were determined. Each value is the mean±SEM of determinations in three independent slides of each animal and three animals of each group. Panels B and C show graphs of the expression of MPK1 mRNA and the ratio of RANKL/OPG as quantified by real-time PCR in cavaria tissue from the same animals. Panel D—Immunohistochemical β-catenin staining of representative sections were counterstained with hematoxylin from metaphyseal area of distal femurs of mice at six weeks of age. (i) vehicle control daily injection for 28 days; (ii) hPTH (1-34) 100 ng/g. b.w daily injection for 28 days; (iii) vehicle control continuous infusion with an osmotic pump; and (iv) hPTH (1-34) continuous infusion at 500 ng/h with an osmotic pump. Panel D is a graph showing the numbers of β-catenin-positive osteoblasts as a percent of total osteoblasts per field that were determined. Each value is the mean±SEM of determinations in three independent slides of each animal and three animals of each group.

Figure 8:
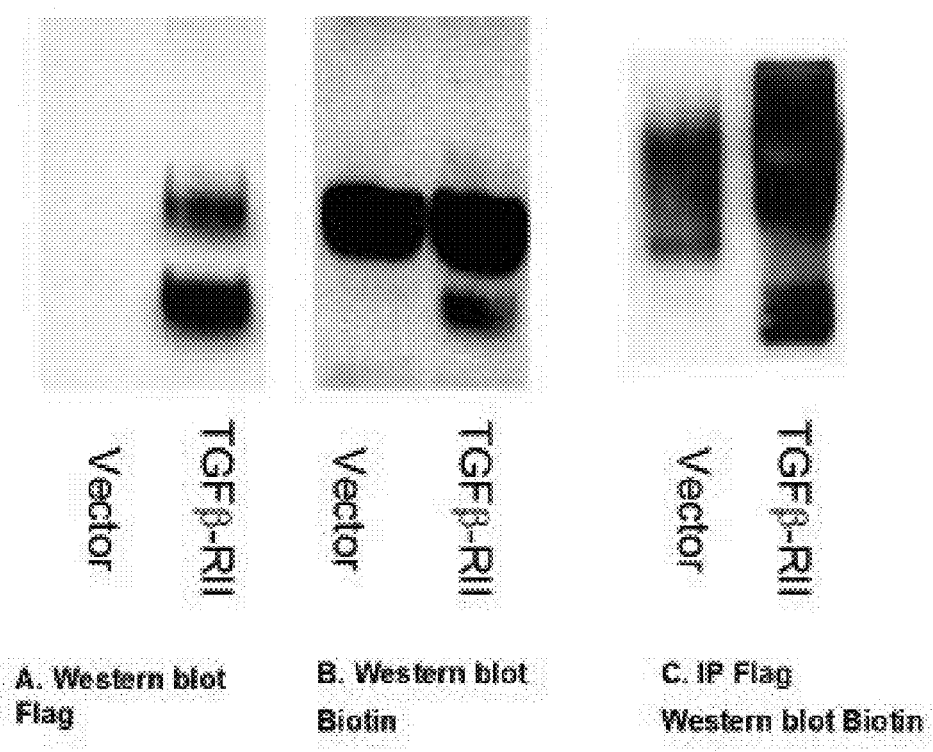

FIG. 8 shows Western blots showing that PTH (1-34) binds to TGFβRII. Embryonic kidney 293 cells were transfected with Flagged TGFβRII expression plasmids or empty vector. The transfected cells were labeled with Biotin-PTH (1-34). Panel A is a Western blot showing the cell lysates from TGFβRII-expressing cells or control cells analyzed with anti-Flag antibodies. Panel B is a Western blot showing the cell lysates from TGFβRII-expressing cells or control cells analyzed with anti-Biotin antibodies. Panel C is a Western blot showing the immunoprecipitation of PTH (1-34) with anti-Flag antibodies, as detected by anti-Biotin antibody on the Western blot.

Figure 9:
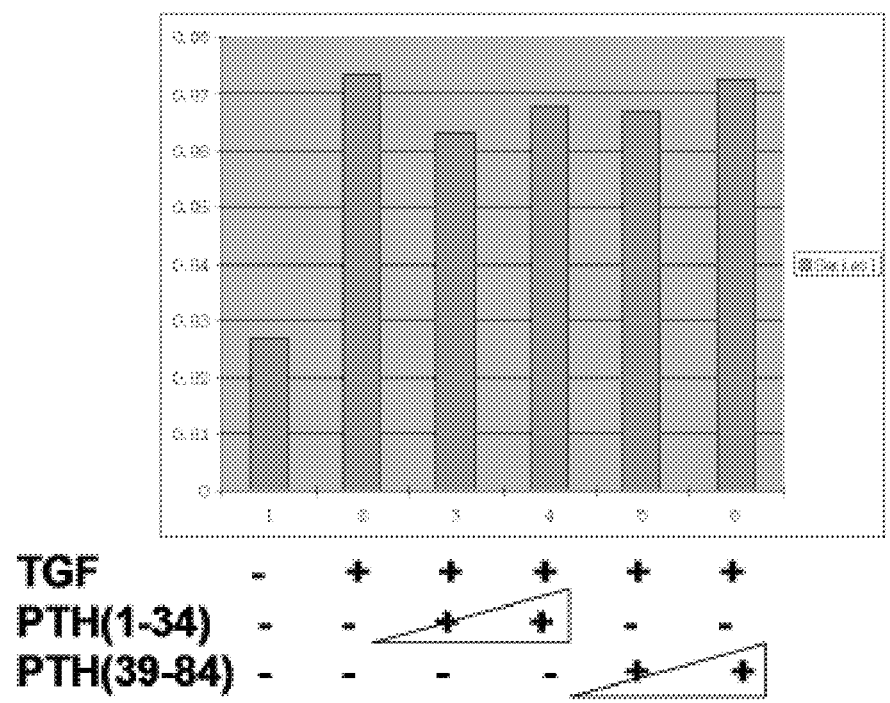

FIG. 9 shows that PTH inhibits TGF-β-induced transcription activity. A Smad binding response luciferase reporter (SBE-luc) was transfected into 293 cells. TGF-β (2 ng/ml) was added in combination with different doses of PTH (1-34) or cPTH (39-84). Twenty-four hours after transfection, the cells were lysed and the luciferase signal was detected. Luciferase values shown in the figures are representative of transfection experiments performed in triplicate in at least three independent experiments. The relative increased fold of the luciferase activity stimulated by TGF-β in each cell line was calculated. The results indicate that both PTH fragments inhibited TGF-β-induced transcription activity.

Figure 10:
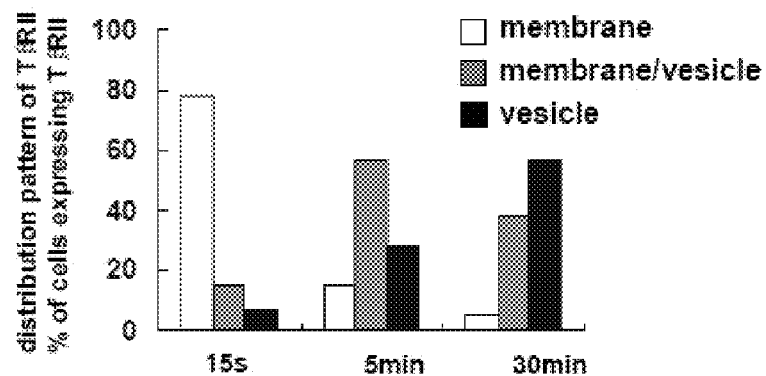
Figure 10:
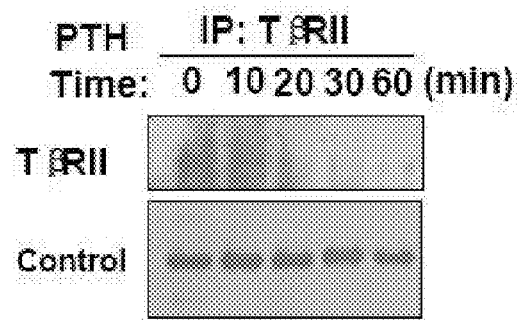
Figure 10:
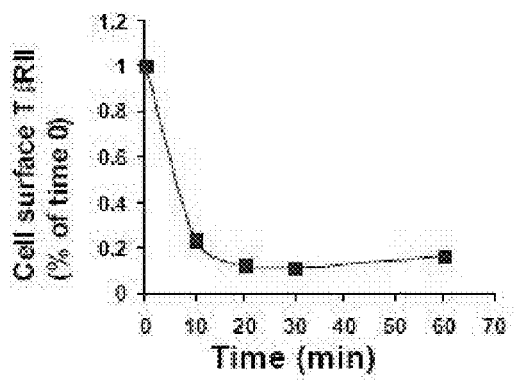

FIG. 10 shows graphs and Western blots demonstrating that PTH induces endocytosis of TGFβRII. TGFβRII tagged with Flag epitope was expressed in HEK293 cells that were expressing PTH1R or not, and the transfected cells were treated with PTH or control. FIGS. 10A and 10B show that TGFβRII molecules were internalized, located inside vesicles, within 30 minutes of treatment with PTH.

FIG. 11A shows a Western blot showing the coimmunoprecipitation of TGFβRII and PTH1R, demonstrating that the PTH induced interaction between the receptors mediates internalization of both receptors. Panel B is a schematic of the interactions taking place in these experiments.

Figure 12:
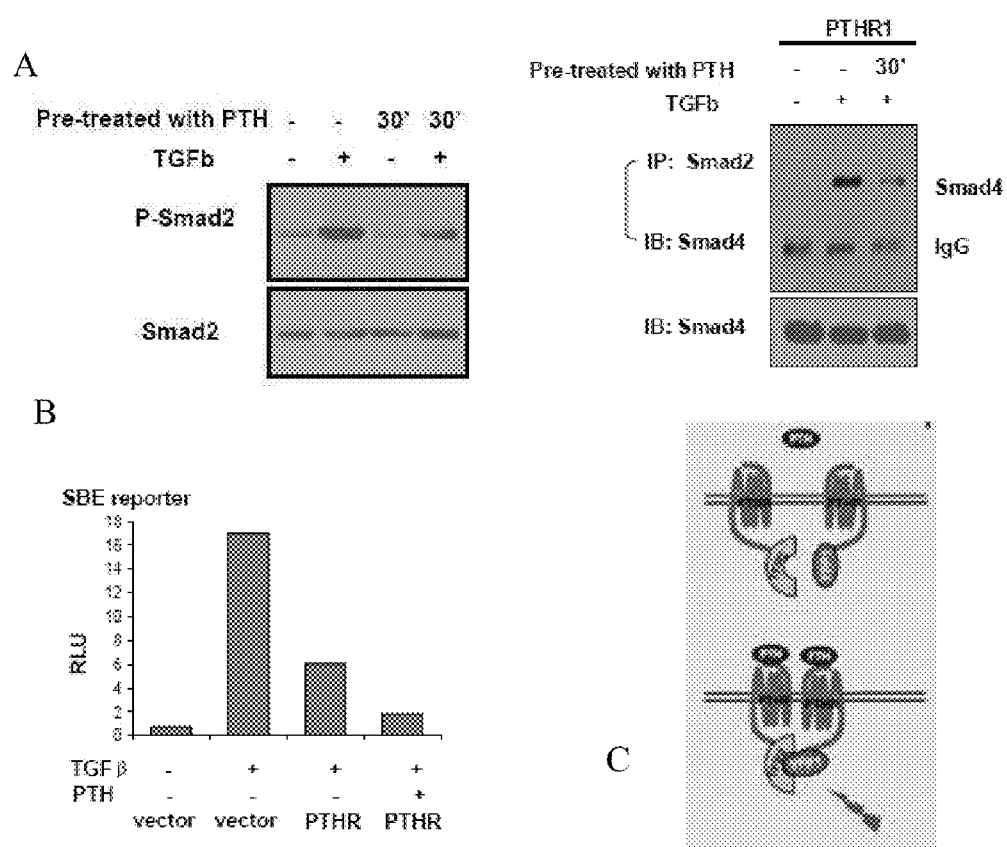

FIG. 12 shows that the complex of TGFβRII and PTH-induced PTHR dimer/polymer internalizes through the arrestin-mediated pathway and attenuates TGFβ/Smad signaling. Panel A shows Western blots showing that phosphorylation of Smad2 was stimulated by TGFβ, and this phosphorylation was inhibited by pre-treatment with PTH. Panel B is a graph showing the decrease in activity from the SBE-luciferase reporter in the presence of PTH and PTH1R. Panel C is a schematic showing the potential dimer interactions of PTH1R polypeptides and shows Western blots demonstrating the inhibitory effect of PTH1R on smad2 interaction with Smad4.

Figure 13:
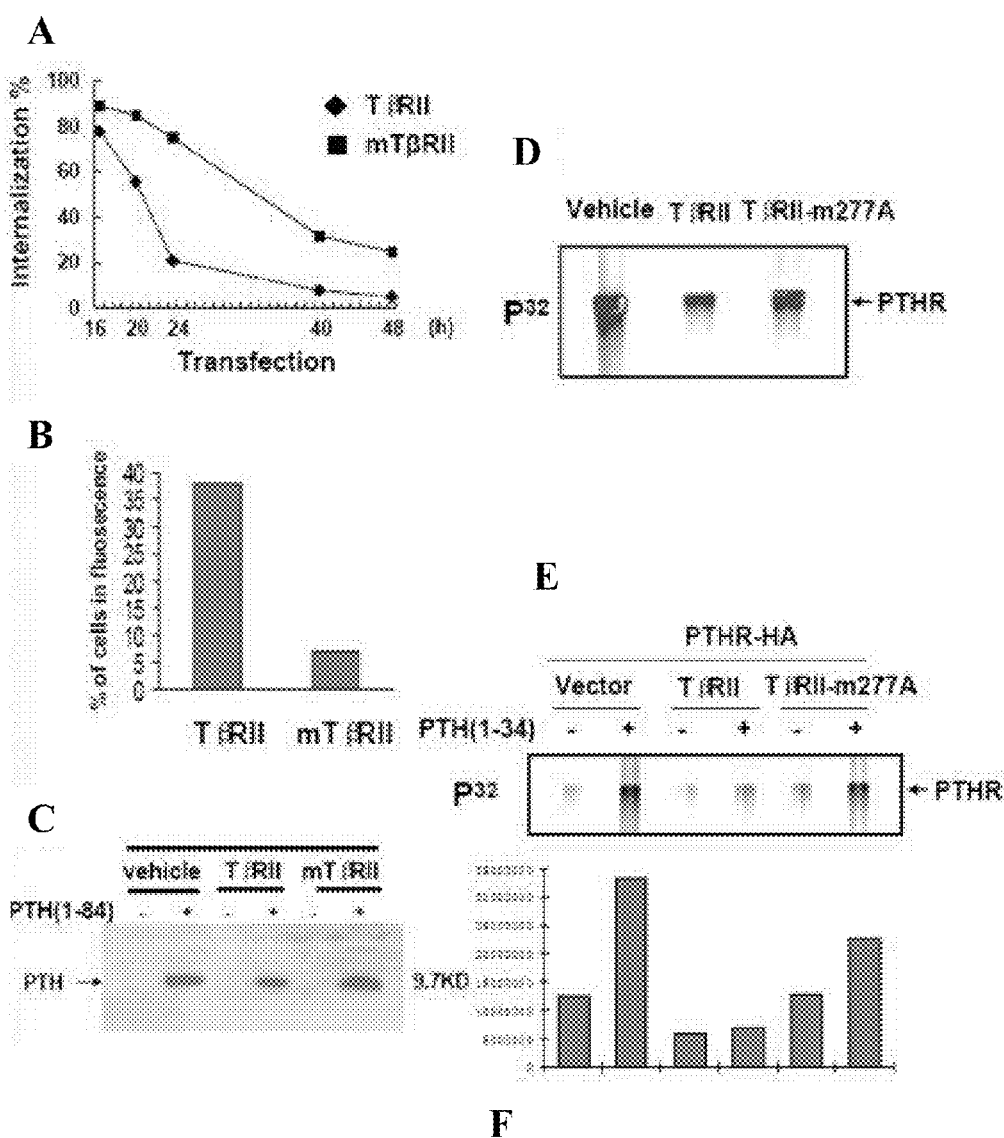

FIG. 13 shows data indicating that the kinase activity of TGFβRII is involved in TGFβRII-mediated endocytosis. Panels A and B are graphs showing that a kinase dead TGF-βRII mutant (K277A) decreased internalization of PTH1R and exhibited decreased PTH1R-TGFβRII interaction (fluorescence). Panel C shows that overexpression of wild type TGFβRII decreased binding of PTH ligands by about 50%, but K277A showed an increase in ligand binding. Panels D and E showed that K277A did not reduce PTH-induced phosphorylation of PTH1R.

Figure 14:
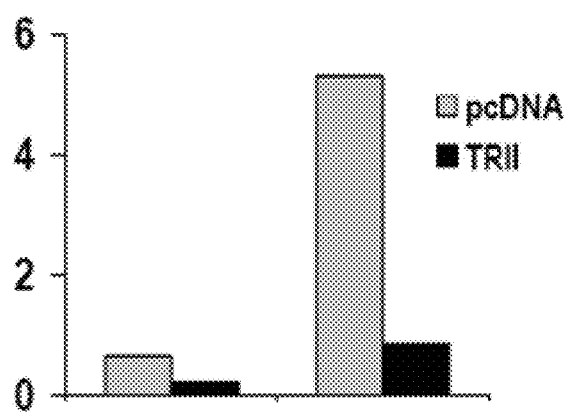
Figure 14:
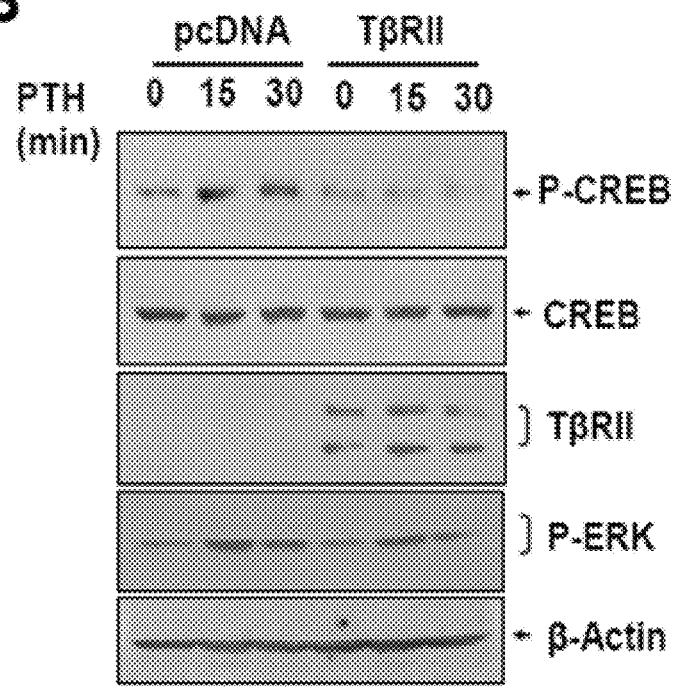
Figure 14:
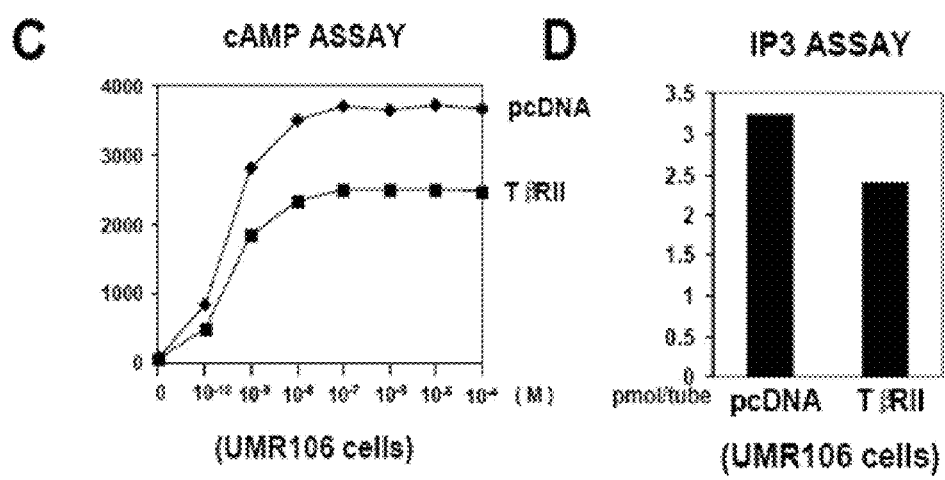

FIG. 14 shows data indicating that TGFβRII reduces PTH-induced activation of cAMP by decreasing membrane PTH1R. FIG. 14A shows that TGFβRII inhibits PTH-induced activation of CREB responsive luciferase activity. FIG. 14B shows that TGFβRII inhibits PTH-induced phosphorylation of CREB. FIG. 14C shows that TGFβRII inhibits PTH induced cAMP. FIG. 14D shows that TGFβRII inhibits PTH-induced IP3 activity.

Figure 15:
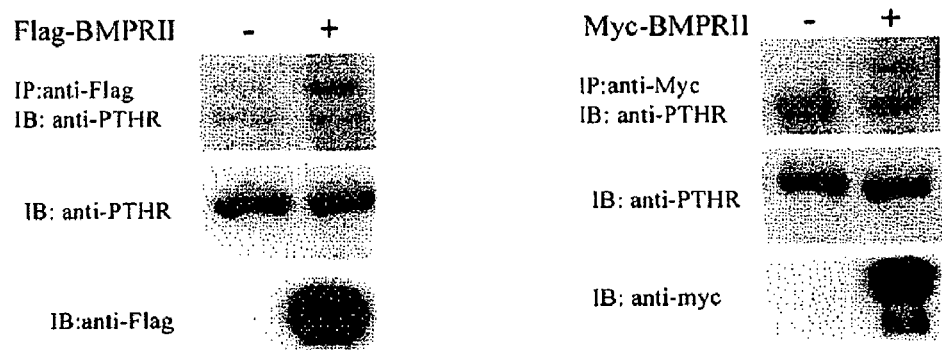
Figure 15:
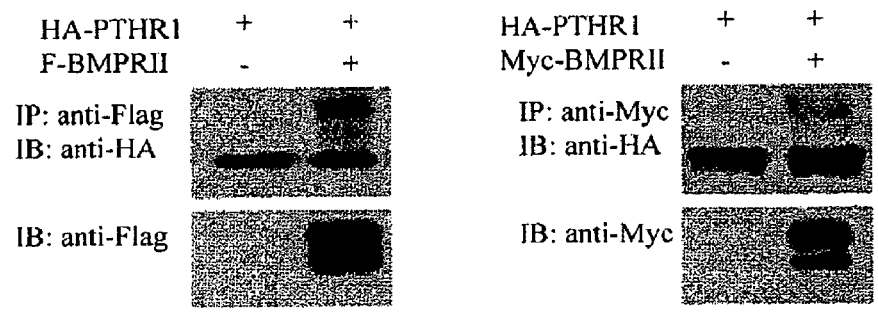
Figure 15:
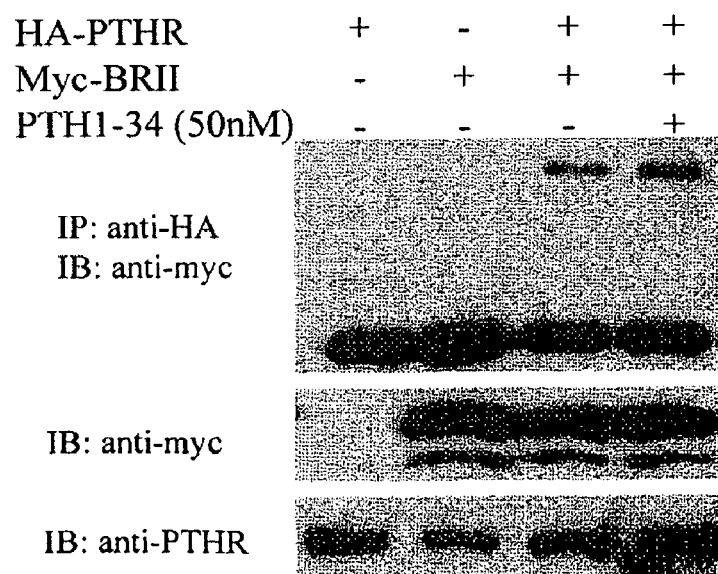

FIGS. 15A, 15B, and 15C show that PTH induces PTH1R interaction with both BMPRII long form and short form. Embryonic kidney 293 cells were transfected with HA-PTH1R and myc-BMPRII long form (15A, 15B and 15C), or Flag-BMPRII short form (15A and 15B) and were treated with vehicle or PTH (1-34) for 24 hours (15C). BMPRII was immunoprecipitated from the cell extracts using anti-Myc or anti-Flag antibodies, and the immunocomplex was detected by Western blotting with HA antibody specific for PTH1R. Alternatively, PTH1R was immunoprecipitated first using anti-HA antibody, and the immunocomplex was detected by Western blotting with anti-Myc and anti-Flag antibodies specific for the BMPRII long and short forms. The results demonstrated that both long and short forms of BMPRII interact with PTH1R (FIGS. 15A and 15B) and that PTH induces the interaction (FIG. 15C).

Figure 16:
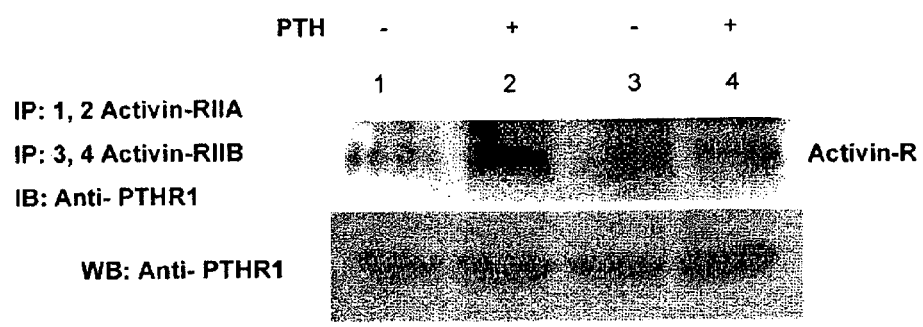

FIG. 16 shows that PTH induces endogenous PTH1R interaction with ActRII and ActRIIB. Embryonic kidney 293 cells were treated with vehicle or PTH (1-34). ActRII and ActRIIB were immunoprecipitated from the cell extracts using anti-ActRII or ActRIIB antibodies, and the immunocomplex was detected by Western blotting with an antibody specific for PTH to detect PTH protein. The results indicate that both ActRII and ActRIIB interact with PTH1R, and PTH enhances the interaction.

Figure 17:
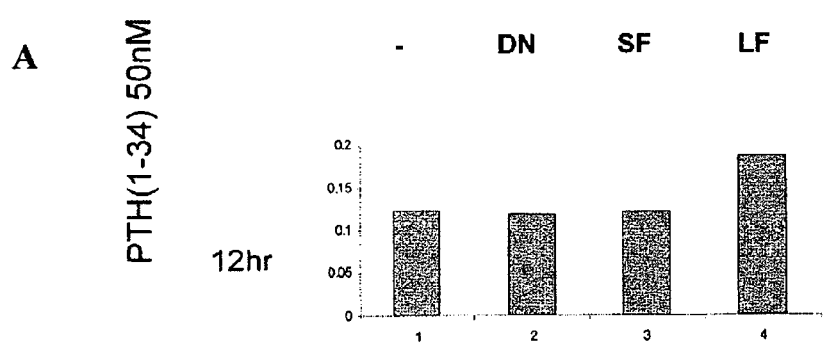
Figure 17:
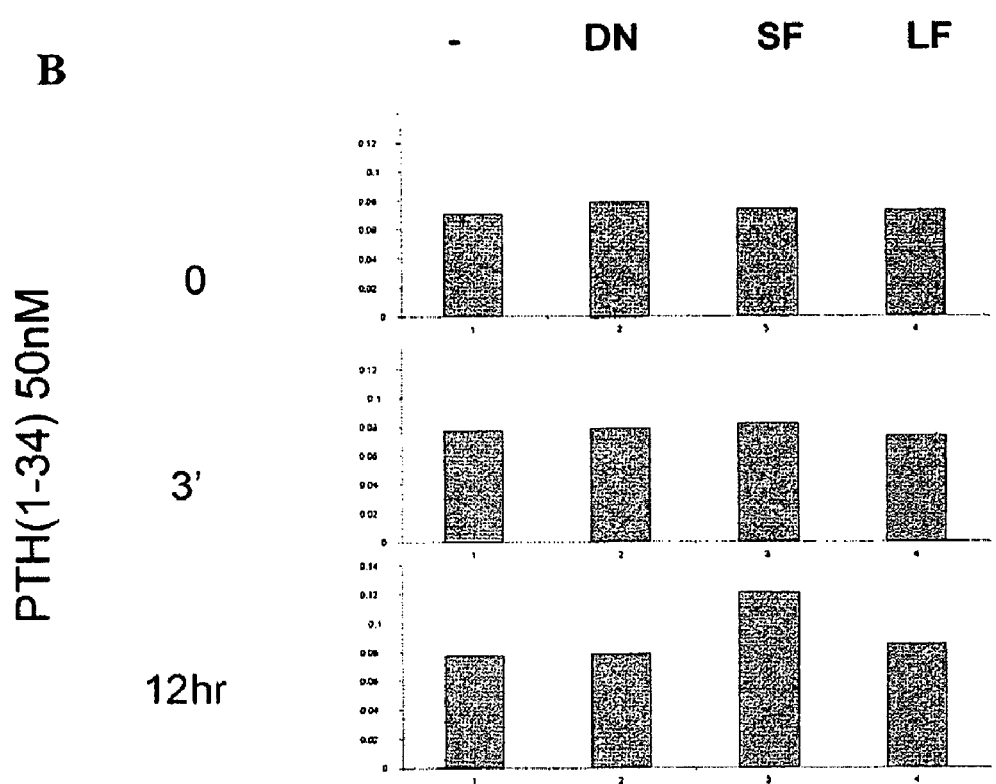

FIGS. 17A and 17B are graphs showing that BMPRII regulates PTH-induced PKA and PKC activity. 293 cells were transfected with BMPRII long form, short form and dominant negative expression plasmids and treated with vehicle or PTH (1-34). The transfected cells were harvested and lysed. PKA (Panel A) and PKC (Panel B) activity were measured.

Figure 18:
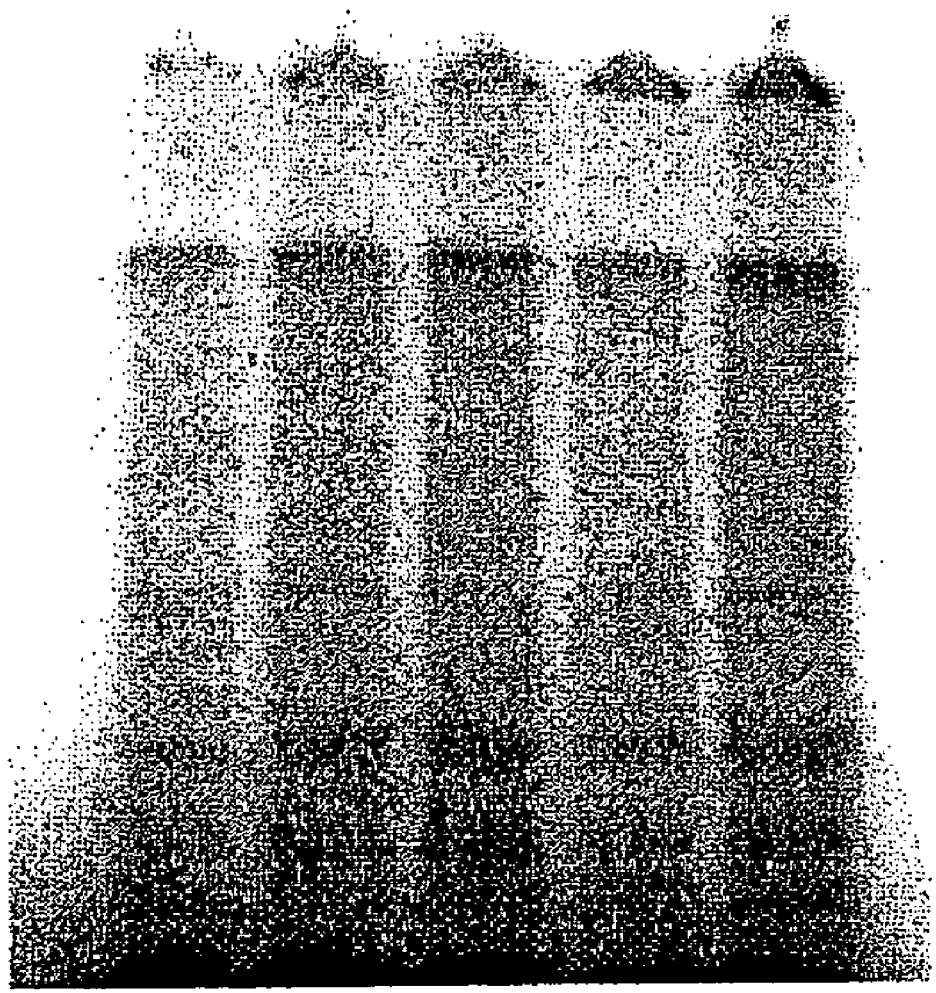

FIG. 18 is a photomicrograph demonstrating that ActRII and ActRIIB enhance binding of PTH (1-34) to its receptors. 293 cells were transfected with ActRII, ActRIIB, BAMBI, or PTH1R expression plasmids, or with empty vector. The transfected cells were photo-labeled with $^{125}$I-PTH (1-34). The cells lysates were analyzed on PAGE and exposed on film.

Figure 19:
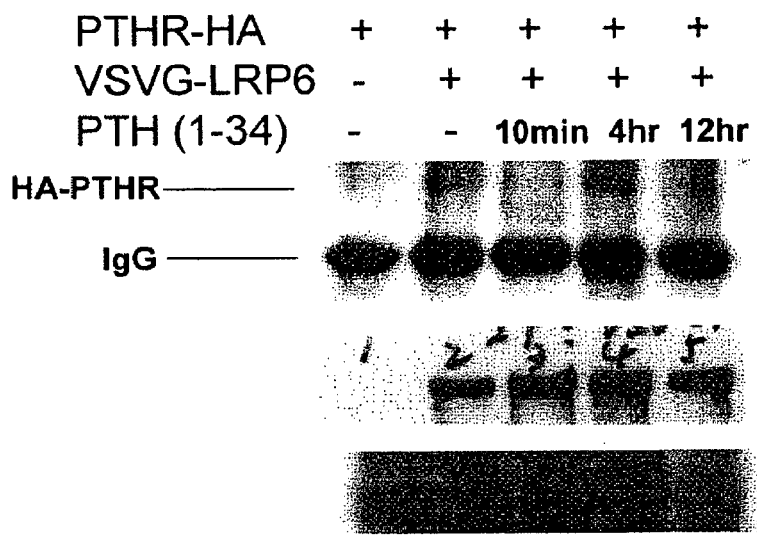
Figure 19:
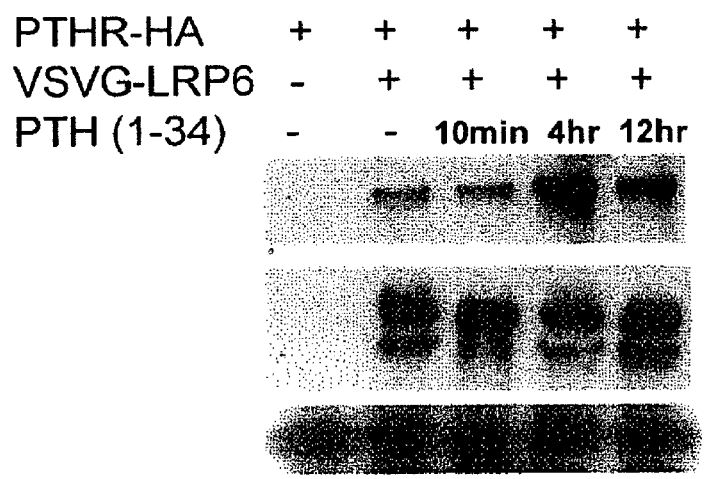

FIG. 19 shows that PTH induces interaction of PTH1R with LRP5/6. Embryonic kidney 293 cells were transfected with HA-PTH1R and VSVG-LRP6, and with vehicle or PTH (1-34) for 10 minutes, 4 hours, or 12 hours (Panels A and B). VSVG-LRP6 was immunoprecipitated from the cell extracts using anti-VSVG antibody (Sigma), and the immunocomplex was detected by Western blotting with HA antibody specific for PTH1R (Panel A). Alternatively, PTH1R was immunoprecipitated first using anti-HA antibody, and the immunocomplex was detected by Western blotting with anti-VSVG antibody specific for LRP6 (Panel B). The results demonstrated that LRP6 interacts with PTH1R and that PTH induces the interaction.

DETAILED DESCRIPTION OF THE INVENTION

The present invention relates to a method for screening for a compound, a PTH polypeptide, and/or a fragment of a PTH polypeptide that is capable of regulating skeletal development through one or more novel PTH receptors selected from the group consisting of low density lipoprotein receptor-related proteins LRP5 and LRP6 (LRP5/6), TGF-β type II receptor (TGFβRII), BMP type II receptors (BMPRII) including long form and short form, Activin type II receptor (ActRII), Activin type II receptor (ActRIIB), and homologs and analogs thereof, collectively referred to herein as "PTH receptors." The present invention particularly relates to a method for screening for compounds, PTH polypeptides, and/or fragments of a PTH polypeptide that are capable of improving bone mass. The TGFβ superfamily, including BMP and activin, regulates many aspects of skeletal development, including osteoblast and chondrocyte differentiation, cartilage and bone formation, mesoderm patterning, and craniofacial and limb development. The identification of the present novel class of receptors for PTH and PTH fragments provides a therapeutic target for treatment for osteoporosis and other bone-related diseases.

The present invention may be understood more readily by reference to the following detailed description of preferred embodiments of the invention and Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

The present invention provides methods of identifying a compound, PTH ligand, or fragment of PTH that improves bone mass, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether an increase in interaction between the cPTH receptor and PTH1R occurs in the cell contacted with the compound, PTH ligand, or fragment of PTH ligand, said increase being an indication that the compound, PTH ligand, or fragment of PTH ligand improves bone mass. In certain embodiments, the test compound, PTH ligand, or fragment of PTH ligand increases Wnt signaling by recruiting LRP5/6, increases β-catenin levels, increases LRP5/6-induced transcription, increases phosphorylation of LRP5/6, and/or increases interaction of axin with LRP5/6. In other embodiments, the test compound, PTH ligand, or fragment of PTH ligand induces PTH1R internalization by recruiting TGFβRII and/or decreases TGFβ-induced transcription. The invention also provides that in certain embodiments, the test compound, PTH ligand, or fragment of PTH ligand increases PKA activity. In one embodiment, the BMPRII is either the BMPRII short form or BMPRII long form.

The present invention provides methods of identifying a compound, PTH ligand, or fragment of PTH ligand that improves bone mass, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether a decrease in translocation of a SMAD occurs in the cell contacted with the compound, PTH ligand, or fragment of PTH ligand, said decrease being an indication that the compound, PTH ligand, or fragment of PTH ligand improves bone mass. In certain embodiments, the test compound, PTH ligand, or fragment of PTH ligand increases Wnt signaling by recruiting LRP5/6, increases β-catenin levels, increases LRP5/6-induced transcription, increases phosphorylation of LRP5/6, and/or increases interaction of axin with LRP5/6. In other embodiments, the test compound, PTH ligand, or fragment of PTH ligand induces PTH1R internalization by recruiting TGFβRII and/or decreases TGFβ-induced transcription. The invention also provides that in certain embodiments, the test compound, PTH ligand, or fragment of PTH ligand increases PKA activity. In one embodiment, the BMPRII is either the BMPRII short form or BMPRII long form.

The present invention provides methods of identifying a compound, PTH ligand, or fragment of PTH ligand that enhances the interaction of PTH1R with a PTH receptor, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether interaction of PTH1R with the PTH receptor is increased in the presence of the test compound, PTH ligand, or fragment of PTH ligand, an increase in said interaction being an indication that the test compound, PTH ligand, or fragment of PTH ligand enhances the interaction of PTH1R with the PTH receptor. In certain embodiments, the test compound, PTH ligand, or fragment of PTH ligand increases Wnt signaling by recruiting LRP5/6, increases β-catenin levels, increases LRP5/6-induced transcription, increases phosphorylation of LRP5/6, and/or increases interaction of axin with LRP5/6. In other embodiments, the test compound, PTH ligand, or fragment of PTH ligand induces PTH1R internalization by recruiting TGFβRII and/or decreases TGF (3-induced transcription. The invention also provides that in certain embodiments, the test compound, PTH ligand, or fragment of PTH ligand increases PKA activity. In one embodiment, the BMPRII is either the BMPRII short form or BMPRII long form.

The present invention provides methods of identifying a compound, PTH ligand, or fragment of PTH ligand that modulates interaction of cPTH and a PTH receptor, comprising the steps of providing a cell expressing a PTH receptor selected from the group consisting of LRP5/6, TGFβRII, BMPRII, ActRII, and ActRIIB; contacting the cell with a test compound, PTH ligand, or fragment of PTH ligand; and determining whether the interaction between one or more of the PTH receptors and cPTH is modulated in the cell contacted with the compound, PTH ligand, or fragment of PTH ligand. In certain embodiments, said modulation is an increase in interaction between cPTH and the PTH receptor. In other embodiments, said modulation is a decrease in interaction between cPTH and the PTH receptor. In certain embodiments, said modulation is an indication that the test compound, PTH ligand, or fragment of PTH ligand is capable of improving bone mass.

The present invention provides processes for making a compound, PTH ligand, or fragment of PTH ligand that improves bone mass, comprising the steps of carrying out one of the methods described herein to identify a compound, PTH ligand, or fragment of PTH ligand that improves bone mass, and manufacturing the compound, PTH ligand, or fragment of PTH ligand. The present invention provides a compound, PTH ligand, or fragment of PTH ligand that increases interaction between PTH1R and a PTH receptor, for use in a medicament for improving bone mass.

The present invention also provides methods of improving bone mass in an individual in need thereof, comprising administering to the individual a therapeutically effective amount of a compound, PTH ligand, or fragment of PTH ligand that increases interaction between PTH1R and a PTH receptor selected from the group consisting of LRP5/6, TGF-βRII, BMPRII, ActRII, and ActRIIB in a bone precursor cell.

The present invention provides methods of improving bone mass in an individual in need thereof, comprising administering to the individual a therapeutically effective amount of a compound, PTH ligand, or fragment of PTH ligand that modulates interaction of cPTH and a PTH receptor selected from the group consisting of LRP5/6, BMPRII, ActRII, and ActRIIB. In certain embodiments, the compound, PTH ligand, or fragment of PTH ligand decreases the interaction of cPTH with the PTH receptor. In other embodiments, the compound, PTH ligand, or fragment of PTH ligand increases the interaction of cPTH with the PTH receptor. The invention provides that in some embodiments of these methods, the individual has a bone-related disorder selected from the group consisting of osteoporosis, rheumatoid arthritis, cancer-induced bone lesions, T-cell or B-cell malignancies, or other cancers or bone disorders.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

Standard techniques for cloning, DNA isolation, amplification and purification, for enzymatic reactions involving DNA ligase, DNA polymerase, restriction endonucleases, and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980

Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press; Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

In one aspect, the present invention provides methods for identifying or evaluating agents capable of modulating a novel PTH receptor selected from the group consisting of TGFβRII, short and long form BMPRII, ActRII, ActRIIB, and LRP5/6, and homologs and analogs thereof, in osteoclasts, osteoblasts, or other cells. These novel PTH receptors are expressed in osteoblasts and their precursors. The methods typically include inducing interaction between PTH1R and one of the novel PTH receptors in a cell or a cell-free system, and detecting the activities of PTH receptor-mediated signaling pathways in the cell or cell-free system, or detecting interaction between PTH1R and one of the novel PTH receptors.

As used herein, the term "fragment of PTH" or "fragment of PTH ligand" refers to a truncated version of PTH. Full-length PTH or PTH ligand is 84 amino acids long, represented as 1-84. A fragment of PTH contains fewer than 84 amino acids. Examples of fragments of PTH ligand are presented herein. As used herein, the term "cPTH" or "cPTH polypeptide" refers to the C-terminal portion of PTH, and includes both endogenous cPTH and synthetic cPTH sequences. In cPTH, at least a portion of the N-terminal region of the polypeptide is absent. Furthermore, the C-terminal of cPTH can also be further truncated. Non-limiting examples of cPTH include peptides having 24, 28, 34, 37, 43, 69, 70, and 71 as the N-terminal amino acid. Further non-limiting examples include 7-84, 11-84, 13-84, 19-84, 24-84, 24-38, 24-54, 28-84, 28-48, 34-84, 37-84, 39-84, 43-84, 52-84, 52-76, 53-84, 53-72, 55-84, 57-84, 60-84, 61-80, 64-84, 69-84, 70-84, and 71-84. As also used herein, the term "PTH receptor," "novel PTH receptor," or "novel cPTH receptor" refers to a novel receptor polypeptide that can interact with cPTH, PTH, or a fragment of PTH.

As used herein, the term "modulator of a PTH receptor" refers to any compound, PTH, or fragment of PTH that increases or decreases the activity of PTH or modulates the activity of at least one molecule downstream of one of the novel PTH receptors identified herein in a cell contacted with the modulator. It is understood that combinations of modulators may be used to elicit the desired effect. It is contemplated that the modulator of a novel PTH receptor may act directly on one of the receptors or may act on a molecule upstream or downstream of receptor to thereby modulate PTH signaling. In one embodiment, the modulator interacts with PTH, fragment of PTH, or the novel PTH receptor to thereby modulate the activity of the novel PTH receptor.

Osteoblasts, during proliferation and differentiation, express several different genes that are regulated by various transcription factors that bind to specific response elements in the promoters of these genes. Osteoblasts originate from mesenchymal progenitors or osteoprogenitor cells that, with the appropriate stimulation, undergo proliferation and differentiate into preosteoblasts and then into mature, functional osteoblasts. In culture, as in vivo, osteoblasts form bone-like mineralized nodules by undergoing three stages of development; proliferation, extracellular matrix maturation, and mineralization. During each stage of development, specific subsets of genes are sequentially expressed or repressed. For example, collagen I is known to be a marker for proliferation, alkaline phosphatase for extracellular matrix maturation, and osteocalcin for mineralization. The regulation of gene expression in osteoblasts during development and differentiation occurs predominantly at the transcriptional level. Several transcription factors and signaling pathways, such as AP-1, Runx2, and β-catenin have been shown to play a major role in the regulation of osteoblast gene expression, phenotype, and ultimately bone formation.

As used herein, the term "osteoblast cell" refers to a terminally or non-terminally differentiated cell derived from a bone precursor cell, wherein the osteoblast cell is at least more differentiated towards an osteoblast phenotype than the cell from which it is derived. As used herein, "osteoblast cells" are characterized by the expression of one or more specific marker transcripts, such as, but not limited to, AP-1 family members, Runx2, Fra-2, alkaline phosphatase, osteocalcin, β-catenin, CCAAT/enhancer binding protein (C/EBP), and ATF4, and may also show matrix deposition, matrix mineralization, and/or cuboidal morphology of the cells. Furthermore, as used herein, the term "terminally differentiated osteoblast" refers to an osteoblast cell that is actively producing and mineralizing bone material.

As used herein, the term "bone precursor cell" refers to a cell that differentiates towards the osteoblast lineage upon treatment with known osteoblast-promoting agents, such as, but not limited to type I collagen, fibrinogen, fibrin, fibrinogen, osteocalcin, osteonectin, TGF-β, 1,25-OH Vitamin D3, basic fibroblast growth factor, or bone morphogenic protein 2. It is preferred that the bone precursor cell express one or more of osteocalcin, osteonectin, or alkaline phosphatase. In a preferred embodiment, bone precursor cells include osteoprogenitor cells or preosteoblasts.

Also, as used herein, producing an osteoblast cell encompasses the production of a cell culture that is enriched for osteoblast cells. In certain embodiments of the present invention, the term "enriched" refers to a cell culture that contains more than approximately 50%, 55%, 60%, 65%, 70%, 75%, 80%, 85%, 90%, or 95% of the desired cell lineage.

Osteoclasts, the principal bone-resorbing cells, play a pivotal role in skeleton development and maintenance. Osteoclasts are derived from mononuclear precursors of monocyte/macrophage lineage upon stimulation of two key factors: monocyte/macrophage colony stimulating factor (M-CSF) and receptor activator of nuclear factor kappa B (RANKL, also known as OPGL/ODF/TRANCE).

As used herein, the term "osteoclast cell" refers to a terminally or non-terminally differentiated cell derived from a mononuclear precursors of monocyte/macrophage lineage, wherein the osteoclast cell is at least more differentiated towards an osteoclast phenotype than the cell from which it is derived. Furthermore, as used herein, the term "terminally differentiated osteoclast" refers to an osteoclast cell that is actively resorbing bone material.

As used herein, the term "osteoclast precursor cell" refers to a cell that differentiates towards the osteoclast lineage upon treatment with known osteoclast-promoting agents, such as, dexamethasone, 1,25-dihydroxyvitamin D3, M-CSF, RANKL, TNF-α, IL-1 and prostaglandin E2. In certain embodiments, the osteoclast precursor cell is a pre-osteoclast, a bone marrow macrophage (BMM), a peripheral monocyte, a spleen monocyte, or an immortalized mouse macrophage cell line, such as, but not limited to, RAW264.6.

Also, as used herein, producing an osteoclast cell encompasses the production of a cell culture that is enriched for osteoclast cells. In certain embodiments of the present invention, the term "enriched" refers to a cell culture that contains more than approximately 50%, 55%, 60%, 65%, 70%, 75%, 80%, 85%, 90%, or 95% of the desired cell lineage.

As used herein, the term "differentiate" refers to the production of a cell type that is more differentiated than the cell type from which it is derived. The term therefore encompasses cell types that are partially and terminally differentiated.

As used herein, the terms "biologically active compound" or "bioactive component" and "bioactive factor" refer to any compound or molecule that induces a progenitor cell to partially or terminally differentiate, wherein said differentiation is due at least in part to modulation of signaling through the cPTH receptor-mediated signaling pathway. While the bioactive compound may be as described below, the term is not limited thereto. The term "bioactive component" as used herein includes within its scope a natural or synthetic molecule or molecules which exhibit(s) similar biological activity.

As used herein, the term "member of the PTH receptor family" refers to molecules that are generally characterized by one of skill in the art as belonging to the family, either due to homology with LRP5/6, TGFβRII, short and long form BMPRII, ActRII, and ActRIIB, or due to similarity in function with the PTH receptors identified herein. In one embodiment, the PTH receptor is encoded by a nucleic acid selected from the group consisting of LRP5/6 as shown in GenBank Accession No. NM_002336, TGFβRII as shown in GenBank Accession Nos. NM_003242 or NM_029575, short form BMPRII as shown in GenBank Accession Nos. Z48923 or NM_007561, long form BMPRII as shown in GenBank Accession Nos. BC067418 or the first 530 amino acids of NM_007561, ActRII as shown in GenBank Accession No. M65287, and ActRIIB as shown in GenBank Accession Nos. NM001106 or M84120.

In a further embodiment, the activity of the member of the novel PTH receptor family is increased or decreased by administration of a modulator of a PTH receptor. In one embodiment, the target cells are contacted with an effective amount of a modulator of the PTH receptor. As used herein, the term "effective amount" of a modulator of the PTH receptor refers to that concentration of the compound, PTH, and/or fragment of PTH that is sufficient to effect differentiation of a target cell towards a desired cell lineage, preferably, towards an osteoblast or osteoclast lineage. The determination of such an effective amount is readily determined by one of ordinary skill in the art.

As used herein when referring to a cell, cell line, cell culture, or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining.

As described above, the invention encompasses modulation of novel PTH receptor-mediated signaling through compounds, PTH polypeptides, or fragments of PTH polypeptides that interact with the receptors of the invention or that interact with one or more upstream or downstream components of their signaling pathways.

Identification of the components of the novel PTH receptor signaling pathway of the invention is readily determined by one of ordinary skill in the art. For example, components that directly interact with the novel PTH receptors identified herein can be isolated using the yeast 2-hybrid system. In certain embodiments, a component of a PTH receptor-mediated signaling pathway is determined using the yeast 2-hybrid system to find a component that directly interacts with the novel PTH receptor, encoded by a nucleic acid selected from the group consisting of TGFβRII as shown in GenBank Accession Nos. NM_003242 or NM_029575, short form BMPRII as shown in GenBank Accession Nos. Z48923 or NM_007561, long form BMPRII as shown in GenBank Accession Nos. BC067418 or the first 530 amino acids of NM_007561, ActRII as shown in GenBank Accession No. M65287, ActRIIB as shown in GenBank Accession Nos. NM001106 or M84120, LRP5/6 as shown in GenBank Accession No. NM_002336, and homologs and analogs thereof.

Interactions between the PTH receptor and the identified components of its signaling pathway can be evaluated by at least co-immunoprecipitation. Roles of the identified components in bone development (i.e., osteoclasteogenesis or osteoblastogenesis) can be determined, for example, by RNA interference (RNAi) as described above. Candidate molecules that play a role in the bone development and/or interact with the novel PTH receptors of the invention are useful for detecting modulation of at least one PTH receptor-mediated signaling pathway.

In addition, the activation of PTH receptor-mediated signaling pathways can be evaluated by monitoring osteoclast formation or function, or by monitoring osteoblast formation or function. Methods suitable for this purpose include, but are not limited to, osteoclastogenesis or bone resportion assays. See, for example, Armstrong et al., 2002, *J. Biol. Chem.*, 277:44347-44356 and Ye et al., 2002, *Nature*, 418:443-44. A typical osteoclastogenesis assay includes introducing a polypeptide of the present invention into an osteoclast precursor cell, such as a bone marrow macrophage or a splenic hematopoietic progenitor cell, followed by adding a ligand to induce oligomerization of the polypeptide, thereby initiating cellular differentiation. Compounds capable of inhibiting or interfering with osteoclast differentiation can be identified by comparing the level of osteoclastogenesis in the presence of the compound to that in the absence of the compound. In many cases, a compound thus identified can reduce osteoclast differentiation or osteoclastogenesis by at least approximately 30%, 40%, 50%, 60%, 70%, 80%, 90%, or 100%. Osteoclast bone resorption assays can also be used to evaluate activities of novel PTH receptor signaling pathways mediated by the novel receptors of the invention. Novel PTH receptor modulators capable of inhibiting osteoclast bone resorption can be identified by comparing the level of bone resorption in the presence of the modulators to that in the absence of the modulators. In many cases, a modulator thus identified can inhibit osteoclast-dependent bone resorption activities by at least approximately 30%, 40%, 50%, 60%, 70%, 80%, 90% or 100%.

The present invention demonstrates that each of the receptors physically interact with PTH1R in immunoprecipitation assays, and each receptor binds to PTH (1-34). However the functions of the three subtypes of the novel receptors are quite distinct. TGFβRII induces the complex TGFβRII and PTH1R internalization, which provides the molecular mechanism of PTH desensitization and explains why intermittent PTH treatment can lead to an increase in bone mass, whereas continuous PTH impairs bone density. Overexpression of TGFβRII also completely blocks PTH-induced PKA and cAMP activity. Long form and short form BMPRIIs enhance PTH-induced PKA activity. ActRII, ActRIIB, and LRP5/6 mediate PTH-induced activation of the Wnt signaling pathway. For example, PTH induces the interaction of Axin with ActRII, ActRIIB, and LRP5/6 as the initial mechanism of Wnt activation. Therefore, these receptors are co-receptors of classical PTH1R, and in addition, their activities may also be regulated by C-terminal PTH.

Further characterization of these novel receptors identified herein will further clarify why continuous PTH treatment decrease bone formation (resulting in bone pain and pathological fractures) and intermittent treatment stimulates bone formation (leading to increases in bone mass and strength with a corresponding decrease in fracture risk). Chronic exposure to high levels of PTH results in a decrease in the number of cellular PTH1Rs by agonist-induced internalization, and a corresponding reduction in the maximal signaling response to the hormone. PTH receptor internalization may be one of the factors that contributes to decreased anabolic response of skeleton to high level continuous administration of PTH, as compared to intermittent treatment. The present invention demonstrates that PTH induces recruitment of TGFβRII to PTH1R as a complex. Interestingly, a recent study reveals that TGFβRII mediates TGF-β type III receptor complex internalization by direct phosphorylation of its cytoplasmic domain. Therefore, characterization of the molecular mechanism of PTH ligand-induced PTH1R internalization may provide one explanation for the different effects on bone formation with intermittent and continuous PTH treatment.

Any detection methodology known in the art may be used to assess interactions between the receptors and substrates that interact with the PTH receptor. These methodologies include, but are not limited to, surface plasmon resonance (e.g., Biacore), radioimmune based assays, and fluorescence polarization binding assays. When performed in the presence of a test compound, the ability of the test compound to modulate (e.g., inhibit or enhance) the protein-protein binding affinity is determined. For example, either the PTH receptor or substrates that interact with the receptor can be labeled with a detectable moiety so that the binding can be measured and the effectiveness of various inhibitors or enhancers judged. The detectable moiety allows for detection by direct or indirect means. Direct means include, but are not limited to luminescence, chemiluminescence, fluorescence, radioactivity, optical or electron density. Indirect means include but are not limited to an enzyme or epitope tag.

A detectable moiety can be a compound or molecule that is distinguishable from the surroundings. The art is replete with examples of detectable moieties that can be used in screening assays. In the present specification, the term "label" is used interchangeably with "detectable moiety." For example, detectable moieties may be any moiety based on luminescence, chemiluminescence, fluorescence, radioactivity, enzymatic reactions, colorimetric, optical or electron density. It is to be understood that the screening assays described herein for identifying test compounds that modulate the protein: protein interaction may employ one or more of the detectable moieties known in the art. The protein can be directly or indirectly labeled with a detectable moiety. Such moieties can be attached or labeled to the protein by any suitable conventional procedure. For instance, the functional groups on amino acid side chains can be reacted with functional groups on a desired moiety to form covalent bonds. Alternatively, the protein can be derivatized to generate or attach a desired reactive functional group. The derivatization can involve attachment of one or more linkers or couplers, such as any of the family of bifunctional coupling reagents available for attaching various molecules to polypeptides (Pierce Chemical Company, Rockford, Ill.).

In many embodiments, homogeneous assay formats are used to determine interactions between polypeptides, such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence. In another aspect, the inventive methods utilize heterogeneous assay formats such as enzyme-linked immunosorbant assays (ELISA) or radioimmunoassays.

One such assay is based on fluorescence resonance energy transfer (FRET) between two fluorescent labels, an energy donating long-lived chelate label and a short-lived organic acceptor. The energy transfer occurs when the two labels are brought in close proximity via the molecular interaction between various motif of the receptors and downstream signaling molecules.

Another useful assay is a bioluminescence resonance energy transfer (BRET), such as that described in Xu et al., 1999, Proc. Natl. Acad. Sci. USA, 96:151. Similar to a FRET assay, BRET is based on energy transfer from a bioluminescent donor to a fluorescent acceptor protein. However, a green fluorescent protein (GFP) is used as the acceptor molecule, eliminating the need for an excitation light source. Exemplary BRET assays include BRET and BRET$^2$ from Packard BioScience (Meriden, Conn.). It is understood that the sequences of the receptors of the invention and downstream signaling molecule may be configured in the assay in any workable manner, such as alternatively labeling either polypeptide with GFP. It is further understood that inhibitors and enhancers of the polypeptide interaction may be identified.

DELFIA® (dissociated enhanced lanthanide fluoroimmunoassay) is a solid-phase assay based on time-resolved fluorometry analysis of lanthanide chelates (see, for example, U.S. Pat. No. 4,565,790). For this type of assay, microwell plates are coated with a first protein. The binding partner is conjugated to europium chelate or cryptate, and added to the plates. After suitable incubation, the plates are washed and a solution is added to dissociate europium ions from solid phase bound protein into solution, thereby forming highly fluorescent chelates with ligands present in the solution, after which the plates are read using a plate reader to detect emission at 615 nm.

Another assay that may be employed is a FlashPlate® (Packard Instrument Company, Ill.) based assay. This assay measures the ability of compounds to inhibit protein-protein interactions. FlashPlates are coated with a first protein, then washed to remove excess protein. For the assay, compounds to be tested are incubated with the second protein, and $I^{125}$ labeled antibody against the second protein is added to the plates. After suitable incubation and washing, the amount of radioactivity bound is measured using a scintillation counter.

Further embodiments include the AlphaScreen™ assay (Packard Instrument Company, Meriden, Conn.). AlphaScreen technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of two polypeptides), the singlet-state oxygen molecules reacts with chemiluminescent groups in the acceptor beads, which immediately transfer energy to fluorescent acceptors in the same bead. These fluorescent acceptors shift the emission wavelength to 520-620 nm, resulting in a detectable signal. Inhibitors of the interaction of the polypeptides will thus reduce the shill in emission wavelength, whereas enhancers of this interaction would increase it.

In one specific embodiment, a screening method of the present invention comprises the steps of forming a composition comprising the novel receptor of the invention, a downstream signaling molecule, and the test compound, PTH, or fragment of PTH; assaying for the level of interaction of the receptor and the signaling molecule; and comparing the level obtained in the presence of the test compound, PTH, or fragment of PTH to that obtained in the absence of the test compound, PTH, or fragment of PTH, such that if the level obtained differs, a compound, PTH, or fragment of PTH that affects the interaction of the two polypeptides, and thus of a PTH receptor-mediated signaling pathway, is identified. Preferably, at least one of the two polypeptides can be labeled with, a detectable moiety. One of the polypeptides can be soluble, and the other can be bound, although alternative assay formats are possible and well known. The test compound can be added to the composition after addition of the two polypeptides, before both polypeptides are added, or after one polypeptide is added and before the other is added. The interaction of the polypeptides that may be influenced by the test compound includes reciprocal binding of the polypeptides. For example, a test compound may partially or completely inhibit binding of the certain motifs of the receptors to the downstream signaling polypeptide. This partial or complete inhibition of binding can be measured in various ways, such as determining the binding constant in the presence and absence of the test compound. In other embodiments, the binding affinity and/or binding avidity between the polypeptides may be measured with and without the test compound.

Any of the above-described methods can be incorporated in high throughput test systems so that large numbers of test molecules can be screened within a short amount of time. The assays can be performed in a variety of formats, including protein-protein binding assays, biochemical screening assays, immunoassays, cell based assays, etc. These assay formats are well known in the art. The screening assays of the present invention are amenable to screening of chemical libraries and are suitable for the identification of small molecule drug candidates, antibodies, peptides, peptidomimetics, and the like. Chemical libraries include commercially available combinatorial chemistry compound libraries from companies such as, but not limited to, Sigma-Aldrich (St. Louis, Mo.), Arqule (Woburn, Mass.), Enzymed (Iowa City, Iowa), Maybridge Chemical Co. (Trevillett, Cornwall, UK), MDS Panlabs (Bothell, Wash.), Pharmacopeia (Princeton, N.J.), and Trega (San Diego, Calif.).

Moreover, combinations of screening assays can be used to find molecules that regulate the biological activity of PTH receptor interactions. In using combinations of various assays to screen for test compounds, PTH polypeptides, or fragments of PTH polypeptides, it is understood that any of the assays described herein may be used in any order and combination. For example, one embodiment may comprise first determining whether a test compound binds to the PTH receptor or modulates the binding between the PTH receptor and a downstream signaling molecule by using an assay that is amenable to high throughput screening. Test compounds identified in this manner are then added to a biological assay to determine biological effects. By observing the effect that test compounds have on the interaction between the PTH receptor and a downstream signaling molecule in various binding assays, on the PTH receptor-mediated activity in biological function tests, or in cell based screens, compounds that are potential therapeutics because they can modulate the interaction between the PTH receptor and a downstream signaling molecule are identified. These compounds will be useful in treating or preventing disease or conditions with which the PTH receptor-mediated signaling is implicated.

Novel PTH receptor modulators can also be identified based on rational drug design. One goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for the PTH receptor or a downstream signaling molecule of the PTH receptor. This could be accomplished by x-ray crystallography, NMR, computer modeling, or by a combination of these approaches. An alternative approach, "alanine scan," involves the random replacement of residues throughout molecule with alanine, and the resulting affect on function determined.

It also is possible to isolate a PTH receptor or downstream signaling molecule specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using any method suitable for producing antibodies, using an antibody as the antigen.

In many cases, an inhibitor identified by the present invention can inhibit the cPTH receptor-downstream molecule binding or consequential biological activity (e.g., osteoclast or osteoblast formation) by at least 30%, 40%, 50%, 60%, 70%, 80%, 90%, or more. Similarly, a stimulator of the present invention can increase the cPTH receptor-downstream molecule binding or consequential biological activity by at least 20%; 30%, 40%, 50%, or more. Those of ordinary skill in the art will recognize that cPTH receptor modulators with different levels of inhibition or enhancement may be useful for different applications (e.g., for treatment of different disease states).

Novel PTH receptor modulators of the present invention can be any type of molecule, such as small molecules, peptide, peptide mimics, or antibodies. Exemplary antibodies amenable to the present invention include, but are not limited to, monoclonal antibodies, mono-specific antibodies, poly-specific antibodies, non-specific antibodies, humanized antibodies, human antibodies, single-chain antibodies, chimeric antibodies, synthetic antibodies, recombinant antibodies, hybrid antibodies, Fab, F(ab')$_2$, Fv, scFv, Fd, dAb, or biologically active fragments thereof. In one embodiment, an antibody of the present invention includes two or more antigen-binding sites, each of which recognizes a different respective motif. In one example, the binding affinity for the motif is at least $10^{-5}$ M$^{-1}$, $10^{-6}$ M$^{-1}$, $10^{-7}$ M$^{-1}$, $10^{-8}$ M$^{-1}$, $10^{-9}$ M$^{-1}$, or stronger.

In one embodiment, the target cells are contacted with an effective amount of a modulator of the novel PTH receptor-mediated signaling pathway. As used herein, the term "effective amount" of a modulator of the novel PTH receptor-mediated signaling pathway refers to that concentration of the compound that is sufficient to affect differentiation of a target cell towards a desired cell lineage, preferably, towards or away from an osteoblast lineage. The desired concentration is readily determined by one of ordinary skill in the art.

As used herein, the term "contacting" (i.e., contacting a cell, e.g. a target cell, with a compound) is intended to include incubating the compound and the cell together in vitro (e.g., adding the compound to cells in culture). The term "contacting" is not intended to include the in vivo exposure of cells to a modulator of the novel PTH receptor-mediated signaling pathway that may occur naturally in a subject (i.e., exposure that may occur as a result of a natural physiological process). The step of contacting the cell with a test compound, PTH, or fragment of PTH can be conducted in any suitable manner.

The compositions and methods described herein have several useful features. For example, the compositions and methods described herein are useful for modeling the stages of bone development. Furthermore, the compositions and methods described herein can also serve for therapeutic intervention in disease states, such as osteoporosis, osteopenia, or other bone-loss or bone density decreasing disorders. For example, compounds that affect the activity of the PTH receptor can be used in a pharmaceutical formulation for the treatment of a disease state, such as, but not limited to osteoporosis, osteopenia, or other bone-loss or bone density decreasing disorders.

The cell types that differentiate from precursor cells after contact with a modulator of the PTH receptor-mediated signaling pathway have several uses in various fields of research and development including but not limited to drug discovery, drug development and testing, toxicology, production of cells for therapeutic purposes as well as basic science research. These cell types express molecules that are of interest in a wide range of research fields. These include the molecules known to be required for the functioning of the various cell types as described in standard reference texts. These molecules include, but are not limited to, cytokines, growth factors, cytokine receptors, extracellular matrix, transcription factors, secreted polypeptides and other molecules, and growth factor receptors. In addition, the cells can be used as a source of nuclear material for nuclear transfer techniques and used to produce cells, tissues, or components of organs for transplant. The test compounds that increase differentiation of osteoblasts also have a number of functions, including but not limited to the treatment of various bone disorders, usefulness in determining the molecular signaling pathways involved in bone development, demineralization, and bone regrowth.

The progression of the target cell culture to the desired cell lineage or response to a test compound can be monitored by quantitating expression of marker genes characteristic of the desired cell lineage as well as the lack of expression of marker genes characteristic of osteoclast progenitor cells and other cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

In some embodiments of the present invention, cells of the desired cell lineage can be isolated by using an affinity tag that is specific for such cells. One example of an affinity tag specific for a target cell is an antibody that is specific to a marker polypeptide that is present on the cell surface of the target cell but which is not substantially present on other cell types that would be found in a cell culture produced by the methods described herein.

As described herein, one aspect of the invention encompasses a method of improving bone mass in an individual having a bone-related disorder, by administering to the individual a therapeutically effective amount of a compound. As used herein, the phrase "bone-related disorder" refers to a disorder wherein bone formation, deposition, or resorption is abnormal. Bone-related disorders include, but are not limited to, osteoporosis, bone fractures, hypercalcemia of malignancy, osteopenia or osteolytic lesions due to bone metastases, periprosthetic osteolysis, familial expansile osteolysis, periodontal disease, tooth loss, rheumatoid arthritis, osteoarthritis, hyperparathyroidism, Paget's disease, osteodystrophy, myositis ossificans, Bechterew's disease, malignant hypercalcernia, bone loss, bone abnormalities due to steroid hormone treatment, bone abnormalities caused by cancer therapeutics, abnormally increased bone turnover, osteomalacia, Bechet's disease, hyperostosis, osteopetrosis, osteogenesis imperfecta, rachitis, immobilization-induced osteopenia, expansile skeletal hyperphosphatasia, and glucocorticoid-induced osteoporosis.

Another aspect of this invention is directed to methods for strengthening a bone graft, inducing vertebral synostosis, enhancing long bone extension, the treatment and promotion of healing of bone fractures and osteotomies, enhancing bone healing following facial reconstruction, maxillary reconstruction and/or mandibular reconstruction in a vertebrate, e.g., a mammal (including a human being), comprising administering to said vertebrate a therapeutically effective amount of a compound of the current invention, a prodrug or a pharmaceutically acceptable salt thereof, or a stereoisomer or diastereomeric mixture of said compound, prodrug or salt. The composition may be applied locally to the site of bone reconstruction or may be administered systemically.

Administration of the compounds of this invention can be via any mode that delivers the compound systemically and/or locally (e.g., at the site of the bone fracture, osteotomy, or orthopedic surgery).

In the methods of the present invention, the compounds described herein and determined using the screening methods described herein, can form the active ingredient, and are typically administered in admixture with suitable pharmaceutically acceptable diluents, excipients, adjuvants or carriers (collectively referred to herein as "carrier" materials) suitably selected with respect to the intended form of administration, that is, oral tablets, capsules, pills, powders, granules, elixirs, tinctures, suspensions, syrups and the like, and consistent with conventional pharmaceutical practices. Likewise, they may also be administered in intravenous (bolus or infusion), intraperitoneal, intranasal, rectal, topical, subcutaneous, intramuscular or transdermal form, all using forms well known to those of ordinary skill in the pharmaceutical arts.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol, and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. When aqueous suspensions are required for oral use, the active ingredient is combined with emulsifying and suspending agents. If desired, certain sweetening and/or flavoring agents may be added. For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous, or partially aqueous solutions (usually in about 0.1% to 5% concentration), otherwise similar to the above parenteral solutions, are prepared.

The compounds can be applied to the sites of bone fractures or osteotomies, for example, either by injection of the compound in a suitable solvent (e.g., an oily solvent such as arachis oil) to the cartilage growth plate or, in cases of open surgery, by local application thereto of the compound in a suitable vehicle, carrier or diluent such as bone-wax, demineralized bone powder, polymeric bone cements, bone sealants, etc. Alternatively, local application can be achieved by applying a solution or dispersion of the compound in a suitable carrier or diluent onto the surface of, or incorporating it into solid or semi-solid implants conventionally used in orthopedic surgery, such as dacron-mesh, gel-foam and kiel bone, or prostheses.

As used herein, the phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other generally recognized pharmacopeia for use in animals, and more particularly for use in humans. Accordingly, suitable pharmaceutically acceptable carriers include agents that do not interfere with the effectiveness of a pharmaceutical composition.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydro-pyrans, polycyanoacrylates, and crosslinked or amphipathic block copolymers of hydrogels.

Methods of preparing various pharmaceutical compositions with a certain amount of active ingredient are known to those skilled in the art. For examples of methods of preparing pharmaceutical compositions, see Remington: The Science and Practice of Pharmacy, Mack Publishing Company, Easton, Pa., 19th Edition (1995).

The instant compounds are also useful in combination with known agents useful for treating bone-related disorders. Combinations of the presently disclosed compounds with other agents useful in treating osteoporosis or other bone-related disorders are within the scope of the invention. A person of ordinary skill in the art would be able to discern which combinations of agents would be useful based on the particular characteristics of the drugs and the disease involved. Such agents include but are not limited to the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH (1-34 or 1-84); calcitonin; Vitamin D or a synthetic Vitamin D analogue; selective serotonin reuptake inhibitors (SSRIs); and the pharmaceutically acceptable salts and mixtures thereof.

The term "administration" and variants thereof (e.g., "administering" a compound) in reference to a compound of the invention means introducing the compound or a prodrug of the compound into the system of the individual in need of treatment. When a compound of the invention or prodrug thereof is provided in combination with one or more other active agents (e.g., a bisphosphonate, etc.), "administration" and its variants are each understood to include concurrent and sequential introduction of the compound or prodrug thereof and other agents.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

When a compound according to this invention is administered into a subject, the daily dosage will normally be determined by the prescribing physician with the dosage generally varying according to the age, sex, weight, and response of the individual patient, as well as the severity of the patient's symptoms, the route of administration; and the particular compound or salt thereof employed. An ordinarily skilled physician, veterinarian or clinician can readily determine and prescribe the effective amount of the drug required to prevent, counter or arrest the progress of the condition.

In one exemplary application, a suitable amount of compound is administered to a mammal undergoing treatment. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three, four, or more times daily. The doses can be administered at intervals such as once daily, once weekly, or once monthly. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Toxicity and therapeutic efficacy of a PTH receptor modulator can be determined by standard pharmaceutical procedures in cell culture or experimental animal models. For instance, the $LD_{50}$ (the dose lethal to 50% of the population) and the $ED_{50}$ (the dose therapeutically effective in 50% of the population) can be determined. The dose ratio between toxic and therapeutic effects is the therapeutic index, and can be expressed as the ratio $LD_{50}/ED_{50}$. In many cases, PTH receptor modulators that exhibit large therapeutic indices are selected.

The data obtained from cell culture assays and animal studies can be used in formulating a range of dosages for use in humans. In one embodiment, the dosage lies within a range of circulating concentrations that exhibit an $ED_{50}$ with little or no toxicity. The dosage may vary within this range depending upon the dosage form employed and the route of administration utilized.

The compositions and methods of the present invention are administered and carried out until the desired therapeutic effect is achieved. The term "until the desired therapeutic effect is achieved," as used herein, means that the therapeutic agent or agents are continuously administered, according to the dosing schedule chosen, up to the time that the clinical or medical effect sought for the disease or condition being treated is observed by the clinician or researcher. For methods of treatment of the present invention, the pharmaceutical composition is continuously administered until the desired improvement in bone mass or structure is observed. In such instances, achieving an improvement in bone mass or a replacement of abnormal bone structure with normal bone structure are the desired objectives. For methods of prevention of the present invention, the pharmaceutical composition is continuously administered for as long as necessary to prevent the undesired condition. In such instances, maintenance of bone mass density is often the objective. Progress of a treatment can be monitored by periodic assessment of disease progression. The progress can be monitored, for example, by X-rays, MRI, or other imaging modalities, synovial fluid analysis, or clinical examination. Non-limiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

As used herein, the term "composition" is intended to encompass a product comprising the specified ingredients in the specified amounts, as well as any product which results, directly or indirectly, from combination of the specified ingredients in the specified amounts. The term "therapeutically effective amount" as used herein means that amount of active compound or pharmaceutical agent that elicits the biological or medicinal response in a tissue, system, animal, or human that is being sought by a researcher, veterinarian, medical doctor, or other clinician.

The terms "treat," "treating," or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms. As used herein, the term "improving" with respect to bone mass includes increasing or maintaining the current bone mass of an individual, and includes slowing the rate of bone loss. As such, the term reducing or inhibiting the resorption of bone in bone-related disorders. As described herein, determining the modulation of a PTH receptor-mediated signaling pathway, or a modulation of osteoblast or osteoclast formation in vitro contact with a compound is predictive that the compound is useful for treating a bone-related disorder, or improving bone mass. The term "bone resorption," as used herein, refers to the process by which osteoclasts degrade bone. As used herein, the term "bone mass" refers to bone mass per unit area, which is sometimes referred to as bone mineral density.

In the present invention, in one aspect, the compounds can be used to inhibit bone resorption, or more specifically to inhibit undesired or abnormal bone resorption. The term "abnormal bone resorption," as used herein means a degree of bone resorption that exceeds the degree of bone formation, either locally, or in the skeleton as a whole. Alternatively, "abnormal bone resorption" can be associated with the formation of bone having an abnormal structure, as in Paget's disease. In another aspect, the compounds can be used to promote bone resorption, or more specifically to resorb undesired or abnormal bone formation. The term "abnormal bone formation," as used herein means a degree of bone formation that exceeds the degree of bone resorption, either locally, or in the skeleton as a whole. The term "bone resorption inhibiting," as used herein, means preventing bone resorption by the direct or indirect alteration of osteoclast formation or activity. Inhibition of bone resorption refers to prevention of bone loss, especially the inhibition of removal of existing bone either from the mineral phase and/or the organic matrix phase, through direct or indirect alteration of osteoclast formation or activity.

A differentiating medium or environment may be utilized to partially, terminally, or reversibly differentiate the bone progenitor cells of the present invention, either prior to, during, or after contacting the bone progenitor cells with a modulator of the PTH receptor. In other embodiments, the differentiation environment comprises plating the cells in an adherent culture. As used herein, the terms "plated" and "plating" refer to any process that allows a cell to be grown in adherent culture. As used herein, the term "adherent culture" refers to a cell culture system whereby cells are cultured on a solid surface, which may in turn be coated with a solid substrate that may in turn be coated with another surface coat of a substrate, such as those listed below, or any other chemical or biological material that allows the cells to proliferate or be stabilized in culture. The cells may or may not tightly adhere to the solid surface or to the substrate. In one embodiment, the cells are plated on matrigel coated plates. The substrate for the adherent culture may comprise any one or combination of polyornithine, laminin, poly-lysine, purified collagen, gelatin, extracellular matrix, fibronectin, tenascin, vitronectin, entactin, heparin sulfate proteoglycans, poly glycolytic acid (PGA), poly lactic acid (PLA), poly lactic-glycolic acid (PLGA) and feeder layers such as, but not limited to, primary fibroblasts or fibroblast cells lines. Furthermore, the substrate for the adherent culture may comprise the extracellular matrix laid down by a feeder layer, or laid down by the target cell or cell culture.

The methods of the present invention contemplate that target cells may be cultured with a feeder cell or feeder layer. As used herein, a "feeder cell" is a cell that is co-cultured with a target cell and stabilizes the target cell in its current state of differentiation. A feeder layer comprises more than one feeder cell in culture. In one embodiment of the above method, conditioned medium is obtained from a feeder cell that stabilizes the target cell in its current state of differentiation. Any and all factors produced by a feeder cell that allow a target cell to be stabilized in its current state of differentiation can be isolated and characterized using methods routine to those of skill in the art. These factors may be used in lieu of a feeder layer, or may be used to supplement a feeder layer.

As used herein, the term "stabilize" refers to the differentiation state of a cell. When a cell or cell population is stabilized, it will continue to proliferate over multiple passages in culture, and preferably indefinitely in culture; additionally, each cell in the culture is preferably of the same differentiation state, and when the cells divide, typically yield cells of the same cell type or yield cells of the same differentiation state. Preferably, a stabilized cell or cell population does not further differentiate or de-differentiate if the cell culture conditions are not altered, and the cells continue to be passaged and are not overgrown. Preferably the cell that is stabilized is capable of proliferation in the stable state indefinitely, or for at least more than 2 passages. Preferably, it is stable for more than 5 passages, more than 10 passages, more than 15 passages, more than 20 passages, more than 25 passages, or most preferably, it is stable for more than 30 passages. In one embodiment, the cell is stable for greater than 1 year of continuous passaging.

With respect to some of the embodiments of differentiation methods described herein, the above-mentioned growth factors are provided to the cells so that the growth factors are present in the cultures at concentrations sufficient to promote differentiation of at least a portion of the target cells to the desired cell lineage. In some embodiments of the present invention, the above-mentioned growth factors are present in the cell culture at a concentration of at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml, or at least about 1000 ng/ml. In certain embodiments of the present invention, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition.

The compound that modulates signaling of the PTH receptor can further be selected from the group consisting of an antisense nucleic acid, receptor decoy, ribozyme, sense polynucleotide, double stranded RNA, RNAi, aptamer, and small molecule antagonist. As used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived. A nucleic acid is also considered isolated if it has been altered by human intervention, or placed in a locus or location that is not its natural site, or if it is introduced into a cell by transfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

Nucleic acid molecules can be isolated using standard molecular biology techniques and the sequence information provided herein. For example, mRNA can be isolated from a cell, and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed. A nucleic acid molecule can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a known nucleotide sequence can be prepared by standard synthetic techniques, e.g., using an automated DNA synthesizer.

In addition to fragments and fusion polypeptides of the nucleic acid molecules, the present invention includes homologs and analogs of naturally occurring polypeptides, including homologs and analogs of the cPTH receptors identified specifically herein. "Homologs" are defined herein as two nucleic acids or polypeptides that have similar, or "identical," nucleotide or amino acid sequences, respectively. Homologs include allelic variants, orthologs, paralogs, agonists, and antagonists of naturally occurring nucleic acids as defined hereafter. The term "homolog" further encompasses nucleic acid molecules that differ from the determined nucleotide sequence due to degeneracy of the genetic code and thus encode the same polypeptide. As used herein, a "naturally occurring" polypeptide refers to an amino acid sequence that occurs in nature. An agonist of a polypeptide can retain substantially the same, or a subset, of the biological activities of the polypeptide. An antagonist of a polypeptide can inhibit one or more of the activities of the naturally occurring form of the polypeptide. Nucleic acid molecules corresponding to natural allelic variants and analogs, orthologs, and paralogs of a nucleic acid sequence can be isolated based on their identity to the known nucleic acids, or a portion thereof, as a hybridization probe according to standard hybridization techniques under stringent hybridization conditions. In an alternative embodiment, homologs of the nucleic acid sequence can be identified by screening combinatorial libraries of mutants, e.g., truncation mutants, for agonist or antagonist activity.

Procedures for introducing a nucleic acid into a cell are well known to those of ordinary skill in the art, and include, without limitation, transfection, transformation or transduction, electroporation, particle bombardment, and the like. In certain embodiments, the nucleic acid is incorporated into a vector or expression cassette that is then introduced into the cell. Other suitable methods for introducing nucleic acids into host cells can be found in Sambrook, et al., Molecular Cloning: A Laboratory Manual. 2nd Ed., Cold Spring Harbor Laboratory, Cold Spring Harbor Laboratory Press, Cold Spring Harbor, N.Y., 1989, and other laboratory manuals such as Methods in Molecular Biology, 1995, Vol. 44, Ed: Gartland & Davey, Humana Press, Totowa, N.J.

As used herein, the term polypeptide refers to a chain of at least four amino acids joined by peptide bonds. The chain may be linear, branched, circular, or combinations thereof. The terms "peptide," "polypeptide," and "protein" are used interchangeably herein. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The invention also provides chimeric polypeptides. As used herein, a "chimeric polypeptide" or comprises at least a portion of a member of the reference polypeptide operatively linked to a second, different polypeptide. The second polypeptide has an amino acid sequence corresponding to a polypeptide which is not substantially identical to the reference polypeptide, and which is derived from the same or a different organism. With respect to the chimeric polypeptide, the term "operatively linked" is intended to indicate that the reference polypeptide and the second polypeptide are fused to each other so that both sequences fulfill the proposed function attributed to the sequence used. The second polypeptide can be fused to the N-terminus or C-terminus of the reference polypeptide.

To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs are at least about 50-60%, preferably at least about 60-70%, and more preferably at least about 70-75%, 75-80%, 80-85%, 85-90%, or 90-95%, and most preferably at least about 96%, 97%, 98%, 99%, or more identical.

For the purposes of the invention, the percent sequence identity between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

As used herein with regard to hybridization for DNA to a DNA blot, the term "stringent conditions" may refer to hybridization overnight at 60° C. in 10×Denhardt's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. In a preferred embodiment, the phrase "stringent conditions" refers to hybridization in a 6×SSC solution at 65° C. As also used herein, "highly stringent conditions" refers to hybridization overnight at 65° C. in 10× Denhardt's solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1× SSC/0.1% SDS. Methods for nucleic acid hybridizations are described in Meinkoth & Wahl, 1984, Anal. Biochem. 138: 267-284; Current Protocols in Molecular Biology, Chapter 2, Ausubel et al. Eds., Greene Publishing & Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993.

Using the above-described methods, and others known to those of skill in the art, one of ordinary skill in the art can isolate homologs of known nucleic acid sequences. One subset of these homologs is allelic variants. As used herein, the term "allelic variant" refers to a nucleotide sequence containing polymorphisms that lead to changes in the amino acid sequences and that exist within a natural population. Such natural allelic variations can typically result in 1-5% variance in a nucleic acid.

Moreover, nucleic acid molecules encoding a polypeptide from the same or other species such as analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov et al., 1997, Science 278(5338):631-637).

In addition to naturally-occurring variants of a sequence that may exist in the population, the skilled artisan will further appreciate that changes can be introduced by mutation into a nucleotide sequence, thereby leading to changes in the amino acid sequence of the encoded protein, without altering the functional activity of the molecule. For example, nucleotide substitutions leading to amino acid substitutions at "non-essential" amino acid residues can be made in a sequence. A "non-essential" amino acid residue is a residue that can be altered from the wild-type sequence without altering the activity of said protein, whereas an "essential" amino acid residue is required for the activity. Other amino acid residues, however, (e.g., those that are not conserved or only semi-conserved in a domain having biological activity) may not be essential for activity and thus are likely to be amenable to alteration without altering activity. As used herein, the term "mutation" includes substitutions, additions, and deletions of nucleotides or amino acids. One or more amino acid substitutions, additions, or deletions can be introduced into the encoded polypeptide by mutating the nucleic acid using standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue is preferably replaced with another amino acid residue from the same side chain family. Alternatively, in another embodiment, mutations can be introduced randomly along all or part of a coding sequence, such as by saturation mutagenesis, and the resultant mutants can be screened for biological activity described herein to identify mutants that retain or do not retain specific biological activity Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame. The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the targeted polypeptide sequence.

The antisense nucleic acid can be complementary to an entire coding strand, or to only a portion thereof. In one embodiment, an antisense nucleic acid molecule is antisense to a "coding region" of the coding strand of a nucleotide sequence. The term "coding region" refers to the region of the nucleotide sequence comprising codons that are translated into amino acid residues. In another embodiment, the antisense nucleic acid molecule is antisense to a "noncoding region" of the coding strand of a nucleotide sequence. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of mRNA, but more preferably is an oligonucleotide that is antisense to only a portion of the coding or noncoding region of an mRNA. For example, the antisense oligonucleotide can be complementary to the region surrounding the translation start site. An antisense oligonucleotide can be, for example, about 5, 10, 15, 20, 25, 30, 35, 40, 45, or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methyl inosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be antisense to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

The antisense nucleic acid molecules of the invention are typically administered to a cell or generated in situ such that they hybridize with or bind to cellular mRNA and/or genomic DNA to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix.

The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic promoter are preferred.

The present invention further provides compositions for RNA interference. In this technique, double-stranded RNA or dsRNA derived from the gene to be analyzed is introduced into the target cell. As used herein, "dsRNA" refers to RNA that is partially or completely double stranded. The dsRNA may have a single stranded overhang at either or both ends of the molecule. This dsRNA is processed into relatively small fragments and can subsequently become distributed throughout the cell. The dsRNA fragments interact, in a cell, with the corresponding endogenously produced messenger RNA, resulting in the endogenous transcript being specifically broken down (Zamore et al. 2000, Cell 101:25-33). This process leads to a loss-of-function mutation having a phenotype that, over the period of a generation, may come to closely resemble the phenotype arising from a complete or partial deletion of the target gene.

The invention provides for a composition comprising a dsRNA that is substantially identical to a portion of a target gene of the target cell genome. In certain embodiments of the foregoing, the target gene is selected from the group consisting of: (a) the polynucleotide sequence encoding TGFβRII, (b) the polynucleotide encoding short form BMPRII, (c) the polynucleotide encoding long form BMPRII (d) the polynucleotide encoding ActRII, (e) the polynucleotide encoding ActRIIB, (f) the polynucleotide encoding LRP5/6, and (g) a polynucleotide that hybridizes under stringent conditions to a polynucleotide as defined in any of (a)-(f). In certain embodiments, the target gene is selected from the group consisting of TGFβRII as shown in GenBank Accession Nos. NM_003242 or NM_029575, short form BMPRII as shown in GenBank Accession Nos. Z48923 or NM_007561, long form BMPRII as shown in GenBank Accession Nos. BC067418 or the first 530 amino acids of NM_007561, ActRII as shown in GenBank Accession No. M65287, ActRIIB as shown in GenBank Accession Nos. NM001106 or M84120, and LRP5/6 as shown in GenBank Accession No. NM_002336.

The invention further provides for a composition comprising a dsRNA consisting of (a) a first stand comprising a sequence substantially identical to 19-49 consecutive nucleotides of the polynucleotide sequence encoding TGFβRII, the short form or long form of BMPRII, ActRII, ActRIIB, or LRP5/6; and (b) a second strand comprising a sequence substantially complementary to the first strand. Preferably, the dsRNA inhibits expression of a protein encoded by a polynucleotide hybridizing under stringent conditions to the polynucleotide sequence encoding TGFβRII, the short form or long form of BMPRII, ActRII, ActRIIB, or LRP5/6. In further embodiments, the dsRNA has a single stranded overhang at either or both ends. The invention provides for a nucleic acid molecule comprising a regulatory sequence operatively linked to a nucleotide sequence that is a template for one or both strands of the claimed dsRNA. In one embodiment, the nucleic acid molecule further comprises a promoter flanking either end of the nucleic acid molecule, wherein the promoters drive expression of each individual DNA strand, thereby generating two complementary RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated by 3 to 500 base pairs, and wherein after transcription, the RNA transcript folds on itself to form a hairpin.

As an alternative to antisense polynucleotides, ribozymes, sense polynucleotides, or double stranded RNA (dsRNA) can be used to reduce expression of a polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff & Gerlach, 1988, Nature 334:585-591) can be used to catalytically cleave mRNA transcripts to thereby inhibit translation. A ribozyme having specificity for a nucleic acid can be designed based upon the nucleotide sequence of the cDNA or on the basis of a heterologous sequence to be isolated according to methods taught in this invention. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. The hybridizing RNAs may be substantially or completely complementary. By "substantially complementary," it is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention. The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art.

A useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: N.Y.). The information from a Northern blot at least partially demonstrates the degree of transcription of the transformed gene. Total cellular RNA can be prepared from cells, tissues, or organs by several methods, all well-known in the art, such as that described in Bormann et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: N.Y.).

As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Liposomally-encapsulated expression vectors can also be used for gene delivery. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., retroviral, lentiviral, adenoviral, adeno-associated viral (AAV), herpes viral, alphavirus, astrovirus, coronavirus, orthomyxovirus, papovavirus, paramyxovirus, parvovirus, picornavirus, poxvirus, or togavirus vectors), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990), including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides.

Another aspect of the invention pertains to isolated polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations in which the polypeptide is separated from some of the cellular components of the cells in which it is naturally or recombinantly produced. In one embodiment, the language "substantially free of cellular material" includes preparations of a polypeptide having less than about 30% (by dry weight) of a contaminating polypeptide, more preferably less than about 20% of a contaminating polypeptide, still more preferably less than about 10% of a contaminating polypeptide, and most preferably less than about 5% a contaminating polypeptide.

When the polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations in which the polypeptide is separated from chemical precursors or other chemicals that are involved in the synthesis of the polypeptide.

The present invention also provides antibodies that specifically bind to a polypeptide, or a portion thereof, as encoded by a nucleic acid described herein. Antibodies can be made by many well-known methods (See, e.g., Harlow and Lane, "Antibodies; A Laboratory Manual," Cold Spring Harbor Laboratory, Cold Spring Harbor. N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, e.g, Kelly et al., 1992, Bio/Technology 10:163-167; Bebbington et al., 1992, Bio/Technology 10:169-175).

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

PTH Activates Wnt Signaling

Figure 1:
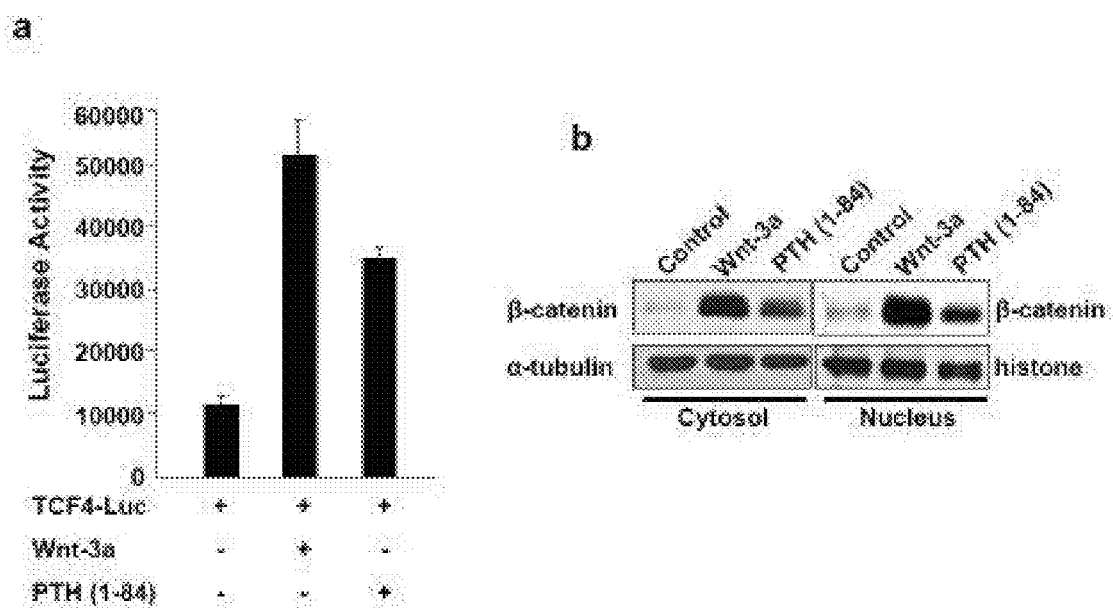
FIG. 1 shows that PTH activates β-catenin signaling. Panel A is a graph showing that PTH stimulates a luciferase reporter with TCF/LEF binding element (TCF4-Luc). Panel B shows Western blots, demonstrating that PTH induces β-catenin stabilization. UMR 106 cells were treated with control medium, conditioned medium containing Wnt-3a and control medium with $5 \times 10^{-7}$ M PTH (1-84) for 30 minutes. Cytosolic and nucleus fractions were prepared and analyzed by Western blotting with specific antibodies against β-catenin, α-tubulin, and histone.

PTH responsive osteoblastic UMR 106 cells were transfected with a Wnt responsive luciferase reporter (TCF4-Luc). Transfected cells were treated with control medium, conditioned medium containing Wnt-3a, or control medium with $10^{-7}$M PTH (1-84) using Lipofectamine Plus reagent (Invitrogen, Cat. No. 10964-013). The luciferase reporter construct TCF4-Luc includes a TCF/LEF binding element. The transfected cells were harvested and lysed 12 hours after transfection, and the luciferase signal was detected using the Dual Luciferase assay kit (Promega) according to the manufacturer's instructions. Luciferase activities were normalized with internal controls, and the results are shown in FIG. 1A. These results indicate that PTH activates the Wnt signaling pathway as indicated by the TCF4-Luc reporter in a manner similar to Wnt-3a. PTH (1-34) also activated the TCF4-Luc reporter (data not shown).

In parallel, proteins from cytosolic and nuclear fractions were isolated from the UMR 106 cells after a 30 minute treatment with control medium, Wnt-3a conditioned medium, or $5\times10^{-7}$ M PTH (1-84). The proteins were transferred to a blotting membrane, and the immunoblots were stained with an anti-β-catenin antibody or antibody to a control protein (α-tubulin or histone). PTH stimulated the levels of β-catenin in both the cytoplasm and the nucleus of the cells (FIG. 1B), suggesting that PTH stabilizes the β-catenin protein and promotes its nuclear translocation. Moreover, cytosolic and nuclear β-catenin protein levels also were examined in embryonic kidney epithelial cells (HEK293) that were treated with different concentrations of PTH and harvested at different time points. These data support the finding that PTH stimulates protein levels of β-catenin in both the cytoplasm and the nucleus in a concentration and time dependent manner.

Example 2

PTH (1-84) Induces Interaction of PTH1R with LRP5/6

In the established canonical Wnt signaling model, Wnt binds to Fz and promotes its oligomerization with a single transmembrane receptor, LRP5/6. Formation of the Fz-LRP5/6 complex is the initial step in stabilizing β-catenin (Tamai et al., 2000, Nature 407:530-535; Semenov et al., 2001, Curr. Biol. 11:951-961). Therefore, PTH was analyzed to determine if it induces recruitment of LRP5/6 to PTH1R to stabilize β-catenin.

To determine if PTH (1-84) induced the formation of a complex of endogenous PTH1R with LRP5/6, an immunoprecipitation assay in osteoblastic UMR-106 cells was used. The cDNA for human LRP6 (Tamai et al., 2000) tagged with VSVG was subcloned into pCS2+, and the cDNA for PTH1R tagged with HA was subcloned into pcDNA3.1. The cell lysates isolated from transfected cells treated with or without PTH were subjected to immunoprecipitation with anti-PTH1R antibodies, and the immunocomplex was detected by Western blotting with a monoclonal antibody that recognizes both LRP5 and LRP6. Conversely, lysates were immunoprecipitated with an anti-LRP5/6 antibody, and the immunocomplex was detected by Western blotting with an antibody specific for PTH1R (data not shown). The results showed that PTH induced the interaction between endogenous LRP5/6 and PTH1R in a time dependent manner (FIG. 2A), reaching its peak in 1 hour (Lane 6). Similar results were obtained with PTH (1-34) (FIG. 19).

Figure 2:
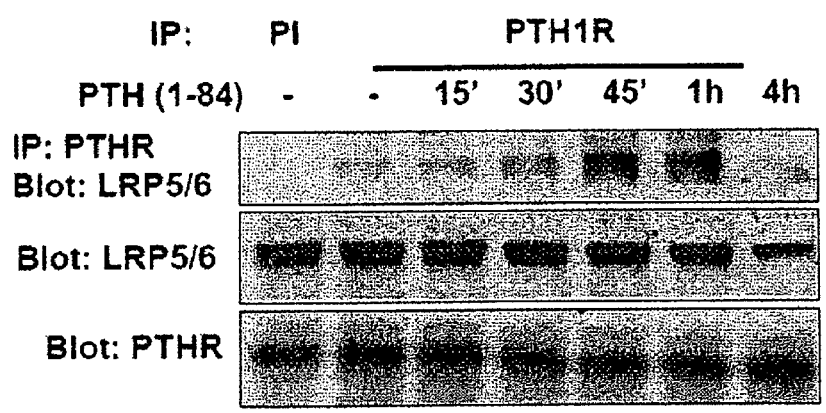
FIG. 2 shows that LRP5 or LRP6 forms a complex with PTH/PTH1R. Endogenous LRP5 or LRP6 was coimmunoprecipitated with PTH1R in UMR 106 cells. UMR 106 cells were treated with $5 \times 10^{-7}$ M PTH (1-84) for indicated times. Panel A shows the results of Western blots, where the PTHR-associated LRP5 or LRP6 was determined by immunoprecipitating the complex with anti-PTHR antibody and blotting with anti-LRP5/6. Panel B shows that LRP6, PTH, and PTH1R form a triple complex. VSVG-tagged LRP6 was cotransfected into HEK 293 cells with HA-PTH1R, and the cells were treated with $5 \times 10^{-7}$ M PTH (1-84) for 1 hour. The LRP6-associated PTH ligand was determined by Western blotting of the anti-VSVG immunoprecipitates. Panel C shows that N-terminal region of LRP6 (LRP6N) interacts with PTHR. VSVG-tagged LRP6, LRP6N, or LRP6C was cotransfected into HEK 293 cells with HA-PTH1R, and the cells were treated with or without $5 \times 10^{-7}$ M PTH (1-84) for 1 hour. The PTH1R-associated LRP6, LRP6N, or LRP6C was determined by Western blotting of the anti-HA immunoprecipitates, and the LRP6-, LRP6N- or LRP6C-associated PTH1R and PTH ligand was determined by Western blotting with an anti-VSVG antibody. Panel D shows that LRP6N disrupts PTH1R/LRP5 or 6 binding. UMR 106 cells were pre-treated with control CM or LRP6N CM followed by $5 \times 10^{-7}$ M PTH (1-84) treatment for 1 hour. The PTH1R- associated LRP6 was determined by Western blotting. Panel E shows the inhibition of PTH-induced TCF4 activation by LRP6N. The effect of LRP-6N on PTH-induced TCF4 activation was determined by luciferase assays.
Figure 2:
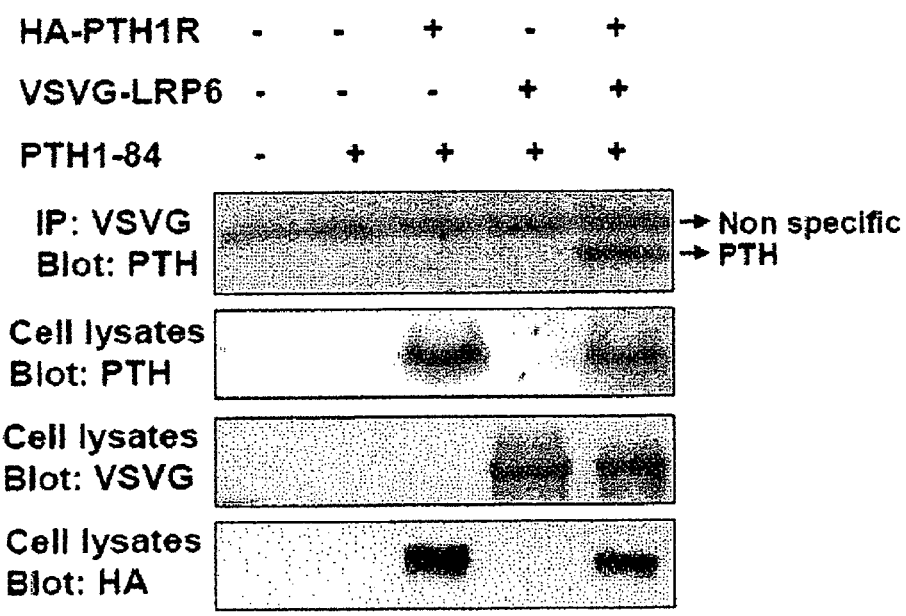
Figure 2:
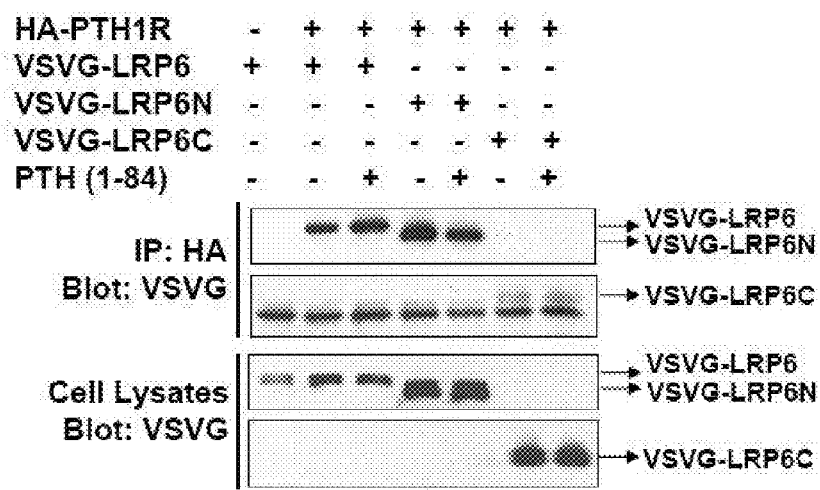
Figure 2:
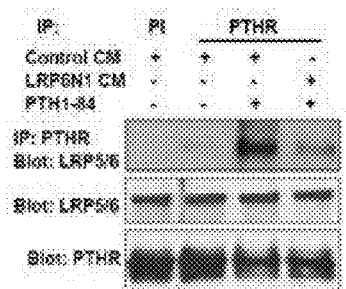
Figure 2:
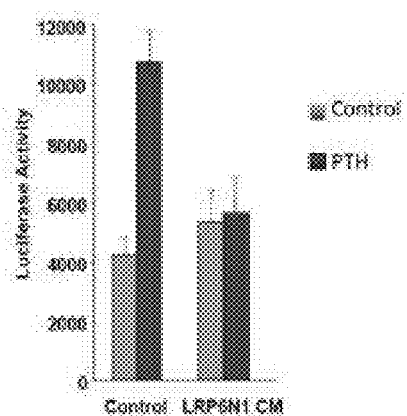

To determine whether the PTH ligand is present in the PTH1R/LRP5/6 complex, further immunoprecipitation assays were performed. The VSVG-tagged LRP6 and/or HA-PTH1R constructs were transfected in cells treated with PTH or vehicle. Cell lysates were immunoprecipitated with an antibody against anti-VSVG, and LRP6-bound immunoprecipitates were detected by Western blotting with anti-PTH antibodies. PTH ligand was immunoprecipitated only when both LRP6 and PTH1R were cotransfected, suggesting the formation of a triple complex (FIG. 2B, lane 5). Unlike 30 kDa Wnt proteins, the longest native PTH is a relative short ligand with only 84 amino acids, which may not able to bind to both PTH1R and LRP5/6. These results suggest that PTH induces recruitment of LRP6 to PTH1R as a complex.

LRP5 and LRP6 mutants lacking the intracellular domain were reported to function as dominant-negative mutants (Mao et al., 2001, Mol. Cell. 7:801-09; Tamai et al., 2004, Mol. Cell. 13:149-56). Therefore, LRP6 without the intracellular domain (LRP6N) was examined to determine whether it interacts with PTH1R and acts as dominant negative. VSVG-tagged full length LRP6, LRP6N, or LRP6 intracellular domain (LRP6C) was co-transfected with HA-PTH1R in 293HEK cells. Cell lysates were immunoprecipitated with anti-VSVG antibodies, and the precipitated complex was detected by Western blotting, using anti-HA antibodies. LRP6N was immunoprecipitated with PTH1R with an apparent affinity similar to the full length LRP6, whereas the interaction between the intercellular domain LRP6C and PTH1R was barely detected (FIG. 2C), suggesting that the extracellular domain of LRP6 mediates the interaction. Thus, PTH ligand is expected to form a triple complex with PTH1R/LRP6N. Moreover, conditioned medium containing LRP6N-IgG was tested for its interaction with PTH1R, and the results again showed the interaction. PTH did not enhance the interaction of PTH1R with LRP6N or LRP6, likely due to overexpression of the receptors (FIG. 2C and data not shown). Finally, LRP6 was shown to inhibit both PTH-induced interaction of endogenous LRP6 with PTH1R and PTH-stimulated TCF-luc activity as a dominant-negative (FIGS. 2D and 2E).

Example 3

PTH Induces Phosphorylation of LRP5/6

Upon association of LRP5/6 to Fz induced by Wnts, LRP5/6 is phosphorylated at the PPPSP motif, thus providing a docking station for Axin, and preventing Axin from participating in β-catenin degradation. Therefore, assays were performed to determine whether the PTH-induced association of LRP5/6 with PTH1R also causes phosphorylation of LRP5/6 at the PPPSP motif.

UMR-106 cells were treated with either PTH or Wnt-3a. The cell lysates were immunoprecipitated for endogenous LRP6, and the precipitated immunocomplexes were detected by Western blotting with an antibody that specifically recognizes the phosphorylated PPPSP motifs (aa, 1490) (Tamai et al., 2004). The results demonstrated that PTH rapidly induced LRP6 phosphorylation at the PPPSP motif (data not shown). To further confirm the role of PTH in inducing phosphorylation of LRP5 and LRP6 individually, HEK293 cells were transfected with HA-tagged LRP5, and the phosphorylated LRP5 was detected by Western blotting of the anti-HA immunoprecipitates with Ab1490. As expected, PTH dramatically stimulated LRP5 phosphorylation at 45 minutes (FIG. 3A, lane 4).

If the observation is true, then the phosphorylated PPPSP motif will serve as an Axin docking site. Indeed, PTH induced binding of Axin to LRP5, and the binding was significantly induced at 30 minutes (data not shown). PTH alone induced much weaker stimulation on the phosphorylation of LRP6 and undetectable Axin/LRP6 binding (data not shown). Both the phosphorylation of LRP6 and the binding of Axin with LRP6 were significantly stimulated by adding GSK3β, but GSK3β alone was not able to stimulate the phosphorylation and binding (FIG. 3B).

These results indicate that similar mechanisms may exist among Wnt-activated events (Zeng and He, 2005). GSK3β is involved in PTH-stimulated LRP6 phosphorylation at its PPPSP motifs. However, the phosphorylation of LRP5 by PTH was very strong and seems GSK3β-unrelated. Since LRP6N, the extracellular domain with transmembrane region, functions as dominant-negative, we examined whether it inhibits PTH-induced Axin binding with LRP5/6. Indeed, LRP6N strongly inhibited the binding of Axin with both LRP5 and LRP6 (FIG. 3C).

Sequential phosphorylation of LRP5/6 at the multiple sites of PPPSP flanking region has been shown as a regulatory mechanism in Wnt canonical signaling pathway. To examine whether PTH also induces sequential phosphorylation of LRP6 in controlling binding of Axin, we generated a construct containing the LRP6 extracelluar domain and transmembrane region with only one intracellular PPPSP motif (LRP6N-PPPSP) and a series of point mutations at the known phosphorylation sites of this single PPPSP motif flanking region (FIG. 3D). PTH induced the binding of Axin to the single PPPSP site, but failed to induce the binding of Axin to the LRP6N 1490m mutant PPPAP (FIG. 3E). In addition, this mutant blocked PTH-stimulated TCF4-luc activation (FIG. 3F). The results indicate that the phosphorylation of PPPSP motif is essential for the binding. However, mutation of any phosphorylation sites mediating Wnt-stimulated LRP6 activity previously identified (Zeng et al., 2005; Davidson et al., 2005) did not affect PTH-induced Axin/PPPSP binding (FIGS. 3E and 3F). These data suggest that phosphorylation of PPPSP may not involve sequential phosphorylation of other sites at its flanking region in Wnt signaling.

Collectively, these results indicate that LRP5/6 recruited to PTH1R by PTH transduces the signal through phosphorylation at its PPPSP motif for Axin binding. However, since PTH plays distinct physiological roles from Wnts, the cellular signals that regulate PTH activity are likely different from Wnts, which is reflected with the distinct phosphorylation pattern of LRP5/6.

Example 4

Activation of PKA and PKC is Required for PTH-Induced Phosphorylation of LRP5/6

Initiation of Gs or Gq leading to activation of PKA or PKC is believed to be the major signaling pathways for PTH function. Therefore, the potential role of PKA or PKC in PTH-activated LRP6/β-catenin signaling was investigated by determining the effects of PKA (H89) and PKC inhibitors (Calphostin C) on PTH-induced Axin/LRP5/6 binding.

Osteoblastic UMR-106 cells were treated with PTH in the presence or absence of the inhibitors. The cell lysates were subject to immunoprecipitation for Axin/LRP6 interaction. Both inhibitors reduced the binding of Axin to LRP6 (FIG. 4A). The inhibition by Calphostin C appears much weaker. If this is the case, inhibitors are expected to block PTH-induced β-catenin stabilization. Western blot analysis showed that both inhibitors reduced β-catenin levels elevated by PTH (FIG. 4B). Calphostin C again is less effective for the inhibition.

Binding of Axin to phosphorylated LRP6 leads to rapid degradation. Then inhibition of Axin/LRP6 binding should enhance degradation of Axin. Indeed, Axin degradation is reduced by both inhibitors (data not shown). TCF/β-catenin luciferase assay showed that both inhibitors reduced β-catenin-mediated transcriptional activity stimulated by PTH (FIG. 4C). To this end, the data demonstrated that PTH induces recruitment of LRP5/6 to PTH1R as the initial step, and the receptor complex formation provides a platform for phosphorylation of LRP5/6 to pass on the signal. PKA and PKC also were examined to determine whether they regulate PTH-induced PTH1R/LRP6 complex formation. Immunoprecipitation experiments demonstrated that neither of the inhibitors affected PTH-induced complex formation of the two endogenous receptors. Apparently, the receptor complex formation is independent of activation of PKA and PKC. Instead, it seems that activation of G protein-mediated PKA and PKC signaling is in parallel with the recruitment of LRP5/6 in PTH signaling. PKA and PKC activity is required for LRP5/6 phosphorylation and Axin/LRP6 binding.

As discussed above, CPTH ligands do not activate PKA, and their functions are not clear. For example, PTH (7-84) binds to PTH1R and induces its internalization without activating the G protein signaling pathway. Thus, the role of the CPTH ligands in inducing phosphorylation of LRP5/6 was investigated, which will also help to verify the role of PKA and PKC in β-catenin signaling. The Axin-LRP6 binding immunoprecipitation assay described above was performed with PTH and CPTH ligands. PTH1-84, PTH1-34, and PTHrP 1-40 stimulated Axin-LRP6 binding, but PTH 7-84 and PTH 79-84 did not (FIG. 5A). TCF/β-catenin luciferase reporter assays also were performed to test whether different C-terminal PTH ligands activate β-catenin signaling since these C-terminal ligands do not induce cAMP synthesis. TCF luciferase activity was significantly elevated by PTH 1-84, PTH 1-34, and PTHrP 1-40, with only a marginal increase by PTH 7-84 and 39-84 (FIG. 5B).

All these results indicate that PTH-induced LRP6/β-catenin activation may be mediated by cAMP/PKA activation. Wnts induce binding of Axin to phosphorylated LRP6, and the membrane-bound Axin undergoes rapid protein dephosphorylation and degradation, which eventually leads to β-catenin stabilization Willert et al., 1999; Yamamoto et al., 1999). LRP6 overexpression significantly reduced Axin protein levels, indicating that LRP6 increased membrane bound-Axin. PTH 1-84, PTH 1-34, and PTHrP 1-40 further down-regulated Axin protein levels; however, PTH 7-84 and PTH 79-84 did not affect Axin level (FIG. 5C).

Example 5

PTH Induces Dorsal Axis Formation Through LRP5/6 and β-Catenin Signaling

LRP5/6 and β-catenin signaling induces dorsal axis formation through activation of responsive genes, such as nodal-related 3 (Xnr3) and siamois (sia) (Tamai et al., 2000). To verify the involvement of PTH/PTHR in LRP5/6-β-catenin pathway, their function in LRP5/6-induced axis formation in xenopus embryos was examined. Ventral injection of either LRP5 or LRP6 RNA into four-cell stage embryos caused very minimal or approximately 30% of dorsal axis duplication (FIG. 6 and data not shown). Coinjection of PTH and PTHR RNA significantly enhanced LRP6-induced axis duplication up to 55%, whereas coinjection of PTH and PTHR in the absence of LRP5 or LRP6 failed to induce axis duplication. Moreover, injection of PTH or PTHR RNA alone failed to elevate LRP5- or LRP6-induced axis duplication, may be because of the low endogenous expression level of PTH or PTHR in *Xenoppus*. In animal pole explants, LRP6 induced Xnr3 and sia expression. Coinjection of PTH and PTHR further increased the Xnr3 and sia level (data not shown).

Example 6

Intermittent Administration of PTH Elevates β-Catenin Level in Osteoblasts Through LRP5/6 for In Vivo Bone Formation β-Catenin, activated by either Wnt or TGF signaling, stimulates proliferation of osteoprogenitors and bone formation. Activation of β-catenin signaling by PTH through recruiting LRP5/6 suggests that β-catenin also mediates PTH-induced bone formation, particularly by intermittent use of PTH. Therefore, the dynamics of β-catenin levels were determined at various time points after a single dose injection of PTH (1-34) in seven-month-old rats. Sections of femur and tibia were immunostained for HE, trichrome, and β-catenin. The first signs of β-catenin expression in osteoblasts appeared at 2 hours after PTH injection, reached a peak at 8 hours, and decreased at 24 hours. Intense staining of β-catenin signal was observed in most preosteoblasts/osteoblasts on the surface of trabecular bone at 8 hours after injection. Specifically, 99.76% of osteoblasts at primary spongliosa subjacent to the epiphyseal growth plates were β-catenin positive, and 89.91% at spongiosa subjacent to diaphyseal hematopoietic bone marrow were β-catenin positive (FIG. 7A).

It has been reported that intermittent PTH treatment targeted proliferating cells in the primary spongiosa of young rat distal femur metaphysis, resulting in an increased number of osteoblasts (Oniya, 1995, Bone). Elevation of β-catenin levels in trabecular bone suggests that β-catenin mediates PTH-induced osteoblast proliferation and bone formation. To ensure that PTH had a specific effect, mRNA levels of PTH target genes, including MPK1, RANKL and OPG were examined using Real-Time PCR. Total RNA was isolated from cavaria bone tissues using the RNeasy mini kit (Qiagen Inc., Chatsworth, Calif.). One µg of total RNA was used for the synthesis of first strand cDNA using the Superscript preamplification system (Life Technologies, Rockville, Md.). Quantitation of MPK1, RANKL, OPG, and GAPDH with specific primers was performed using a DNA Engine Opticon continuous fluorescence detection system (MJ Research, Logan, Utah) with SYBR Green I as the method of detection. Details of the method are as previously described (Wan et al., 2004). Briefly, quantitative PCR was performed in a total reaction volume of 20 µl per capillary for the LightCycler format. This reaction mix contained 10 µl of a SYBR Green mix, 0.5 to 10 pmol of each forward and reverse primer, 2 µl of cDNA, and nuclease-free water to makeup the reaction volume. Runs were performed in duplicate and mean values were subsequently used for analysis. To ensure unbiased analysis, real-time quantitative PCR was performed blindly, and the identity of the samples was only revealed after mRNA measurements had been made. Primers used were as follows: MPK1: forward, 5'-TGGAGGACAACCACAAGGCA-3' (SEQ ID NO:1) and reverse, 5'-TGGCAGTGCACAAA-CACCCT-3' (SEQ ID NO:2); RANKL: forward, 5'-GGT-GAGGAAATTAGCGTCCA-3' (SEQ ID NO:3) and reverse, 5'-TCGAGAGAGGACCGTGAGTT-3' (SEQ ID NO:4); OPG: forward, 5'-CCTCTTTCTTTCTGCCTCTGAT-AGTC-3' (SEQ ID NO:5) and reverse, 5'-CCAAGTCTG-CAACTCGAATCAAAT-3' (SEQ ID NO:6); β-catenin: forward, 5'-GATTAACTATCAGGATGACGCG-3' (SEQ ID NO:7) and reverse, 5'-TCCATCCCTTCCTGCTTAGTC-3' (SEQ ID NO:8); GAPDH: forward, 5'-TAAAGGGCATC-CTGGGCTACACT-3' (SEQ ID NO:9) and reverse, 5'-TTACTCCTTGGAGGCCATGTAGG-3' (SEQ ID NO:10). PTH stimulated MPK1 mRNA expression in osteoblasts isolated from rat injected with PTH, and the ratio of RANKL/OPG, which decreases in Wnt signaling, was increased with PTH injection (FIGS. 7B and 7C). The results showed that PTH had a direct effect.

To further examine whether LRP5/6 mediates PTH-elevated β-catenin levels in vivo, trabecular bone sections were immunostained with the antibody against phosphorylated PPPSP motif. Formalin-fixed tissue sections of 5 μm thickness were deparaffinized in xylene and rehydrated in graded alcohols. Antigen retrieval was achieved by incubating tissue sections in boiling 10 mmol/L citrate buffer (pH 6.0) for 5 minutes in a microwave oven. All sections were then incubated with hydrogen peroxide for 5 minutes. Subsequently, sections were incubated with the primary antibodies against β-catenin or LRP6 1490 for 1 hour at room temperature. After rinsing the primary antibody in T-PBS, antibody detection was accomplished using the Super Sensitive biotin-streptavidin horseradish peroxidase detection kit (Biogenex, San Ramon, Calif.). The diaminobenzidine tetrachloride Super Sensitive substrate kit (Biogenex, San Ramon, Calif.) was used to visualize the antibody-antigen complex. The sections were then counterstained with hematoxylin. Appropriate negative controls, consisting of tissue sections of each case processed without the addition of primary antibody, were prepared along with positive multitissue control sections. Only those cases with greater than 10% immunohistochemical stains were considered as positive. Assessment of the immunohistochemical staining was performed independently by two pathologists. Contrasting results were discussed until an agreement was reached.

These data demonstrated that PTH enhanced phosphorylation of LRP5/6 in preosteoblasts/osteoblasts at the surface of trabecular bone, starting at 2 hours after PTH injection, reaching a peak at 8 hours, and disappearing at 24 hours (data not shown). The pattern of phosphorylated LRP5/6 was correlated with the changes of β-catenin levels induced by PTH in Rat osteoblasts. Total LRP5/6 protein level in osteoblasts of rat tibia bone remained unchanged (data not shown). The observation indicates that PTH recruits LRP5/6 and results in phosphorylation at the PPPSP motif, activating β-catenin signaling in rat bone tissue.

The role of β-catenin in PTH-induced bone formation was then examined. PTH stimulates bone formation when injected daily, i.e. intermittent injection, but causes severe bone loss when infusion continuously. Mice were injected either daily or continuously by infusion with an osmotic pump for 28 days. Bone mineral density was significantly increased in mice with single dose PTH (1-34) daily injection, and decreased when PTH continuous infusion decreased (data not shown). Osteoblast numbers per square millimeter tissue area (N. Ob/T.Ar) increased in the primary spongiosa of the mice femur, and BrdU labeling indicated that osteoblast proliferation was stimulated with PTH daily injection whereas PTH continuous infusion reduced proliferation (data not shown). Similar results were obtained in double labeling. The mineralization in the trabecular and cortical bone matrix also increased in PTH intermittent injected mice by von Kossa assays (data not shown). Most importantly, immunostaining of β-catenin in trabecular bone demonstrated that PTH intermittent injection significantly increased β-catenin in osteoblasts and PTH continuous infusion reduced the level of β-catenin in comparison with control. The percentage of β-catenin positive osteoblasts in PTH intermittent injected mice (96.03%) was much higher than those from untreated control (12.36%) or PTH continuous injected mice (23.54%) (FIG. 7D), whereas the levels of β-catenin remained barely detectable in osteocytes, osteoclasts, and bone marrow cells (data not shown). These data suggest that intermittent administration of PTH elevates β-catenin protein, which accounts for the anabolic bone formation.

Example 7

PTH (1-34) Induces Endogenous PTH1R Interaction with TGFβRII

Human embryonic kidney 293T cells in DMEM with 10% serum were treated with vehicle (water), TGF-β (2 ng/ml), or PTH (1-34) (50 nM) for 24 hours. The 293T cells endogenously expressed TGFβRII. The cells were cultured in DMEM with 10% serum and were split at 30%-40% confluent.

Immunoprecipitation assays were performed as described previously (Shi et al., 2004, J. Cell. Biol. 164:291-300). TGF-βRII was immunoprecipitated from the cell extracts using anti-TGFβRII antibody (Santa Cruz Biotechnology, Inc.; 1:250 dilution), and the immunocomplex was detected by Western blotting with an antibody specific for PTH1R (Santa Cruz Biotechnology, Inc.; 1:200 dilution) to detect PTH1R protein. The results clearly demonstrated that PTH induces interaction between TGFβRII and PTH1R (data not shown). Furthermore, the interaction of PTH1R with TGFβRII can be in the form of monomers or dimers.

Similarly, embryonic kidney 293 cells were transfected with Flag-TGFβRII expression plasmids or empty vector (pcDNA3 vectors) using Lipofectamine Plus reagent (Invitrogen, Cat. No. 10964-013). The transfected cells were labeled with Biotin-PTH (1-34) (Biochem Inc.), and the cells were cultured in DMEM with 10% serum, split at 30%-40% confluent. The cell lysates were analyzed for TGFβRII expression (FIG. 8A) and the binding of Biotin-PTH to TGF-βRII FIG. 8B) by Western blot. Alternatively, the cell lysates were immunoprecipitated as described previously (Shi et al., 2004, J. Cell. Biol. 164:291-300) with anti-Flag M2 antibodies (Sigma F-3165; 1:1000 dilution) and detected by Western blot using ECL Plus Western blotting detection system (RPN2132) (Amersham) (FIG. 8C). These results demonstrate that PTH (1-34) interacts with TGFβRII.

Example 8

PTH Inhibits TGF-β-Induced Transcription Activity

FIG. 9 shows that PTH inhibits TGF-β-induced transcription activity.

A Smad binding response luciferase reporter (SBE-luc) was introduced into the multi-cloning site of pcDNA3 (Invitrogen), and the resulting vector was transfected into 293 cells using Lipofectamine Plus reagent (Invitrogen, Cat. No. 10964-013). TGF-β (2 ng/ml) was added in combination with different doses of PTH (1-34) (50 nM) or cPTH (39-84) (50 nM). The cells were cultured in DMEM with 10% serum and were split at 30%-40% confluent. Forty-two hours after transfection, the cells were lysed, and the luciferase signal was detected using the Dual Luciferase assay kit (Promega) according to the manufacturer's instructions.

Luciferase values shown in the figures are representative of transfection experiments performed in triplicate in at least three independent experiments. The relative increased fold of the luciferase activity stimulated by TGF-β in each cell line was calculated. The results indicate that both N-terminal and C-terminal fragments of PTH inhibited TGF-β-induced transcription activity.

Example 9

TGFβRII is Internalized in Response to PTH Stimulation

PTH has been shown to exhibit a significant functional overlap in activation of downstream signals with TGF-β in many different tissues. In particular, TGFβ1 treatment increases the number of cell membrane PTH1R. Therefore, the potential functional relationship of PTH with TGFβRII was examined. TGFβRII tagged with Flag epitope was transiently expressed in embryonic kidney 293 (HEK293) cells or HEK293 cells stably expressing PTH1R with HA (HEK293-PTH1R). In the absence of PTH, TGFβRII was present predominantly at the cell surface, with a few puncta in the cytosol (data not shown). When the cells were stimulated with PTH (1-34), TGFβRII was internalized in HEK293-PTH1R cells, but not in HEK293 cells. To visualize the effect of PTH to the TβRII, a red fluorescent PTH (1-34) was synthesized in which the TMR fluorophore was attached to the side chain of the lysine residue at position 13 in PTH (1-34) ($PTH^{TMR}$). Following treatment of the cells with $PTH^{TMR}$, TβRII rapidly associated and colocalized with $PTH^{TMR}$ in coated pits at 15 seconds and moved into the intracellular vesicles at 5 minutes to 30 minutes. The amount of cell-surface TGFβRII observed was largely decreased (data not shown).

To quantitate these observations, the cells were fixed at various time points and classified as three types: (1) TGFβRII is dominantly present at the cell surface, (2) TGFβRII locates to both the cell surface and vesicles in the cytosol, and (3) TGFβRII mainly localizes to the cytosol as vesicles. Before stimulation with PTH, TGFβRII was present at the cell surface in 90% of the cells. When the cells were stimulated with PTH for 30 minutes, cells exhibiting cell-surface localization of TGFβRII decreased to less than 10% and percentage of cells in which TGFβRII was observed as cytoplasmic vesicles increased (FIG. 10A). These results were confirmed by measuring the levels of TGFβRII on the plasma membrane by cell-surface biotinylation. From 10 to 30 minutes after stimulation with PTH (1-34), cell-surface TβRII levels were reduced, indicative of receptor clearance from the cell surface membrane (FIG. 10B). Importantly, more than 90% internalized TβRII colocalized with $PTH^{TMR}$ in the cytoplasmic vesicles.

To exclude the possibility that PTH-induced endocytosis of membrane debris causes the modulation of TβRII, the potential interaction between TβRII and PTH ligands was examined by measuring Fluorescence Resonance Energy Transfer (FRET). GFP protein was fused into the end of cytoplasmic, tail of TGFβRII (TβRII-GFP). The principle of FRET strategy allowed the examination of the energy transfer from GFP to TMR when the interaction between TβRII and PTH brings the two fluorophore into close proximity (data not shown). TβRII-GFP was transiently expressed in HEK293-PTH1R cells. Then, 5 minutes after treatment of $PTH^{TMR}$, 10% FRET efficiency was detected in the bleached area (on the membrane and membrane-proximal area) even though the plasma membrane separates two fluorophores. In contrast, only 1.5% FRET efficiency in background was detected in the unbleached area, indicating the direct interaction of PTH with TβRII (data not shown). Therefore, upon PTH stimulation, TβRII acts as a receptor that associates and internalizes with PTH ligand.

Example 10

PTH-Inducible Interaction Between TGFβRII and PTH1R

Since PTH-induced TβRII endocytosis does not occur in HEK293 cells, the possible requirement of PTH1R was then examined. A yellow fluorescent protein (YFP)-based protein-fragment complementation assay (PCA) was employed (Remy et al., 2004). YFP1 fragment was fused into the C-terminal of TβRII. YFP2 fragment was fused into the C-terminal of PTH1R. The PCA strategy was to facilitate visualization of the PTH1R-TβRII interaction through reconstituted YFP in living cells when the interaction brings the complementary fragments of the YFP into close proximity. Expression of TβRII-YFP1 and PTH1R-YFP2 alone or both did not generate fluorescence (data not shown). PTH (1-34) induced YFP fluorescence on the plasma membrane when both TβRII-YFP1 and PTH1R-YFP2 were expressed, whereas, TGF-β1 did not show such an effect, indicating TβRII interaction with PTH1R in response to PTH stimulation only.

The $PTH^{TMR}$ was then employed in the PCA experiment. The colocalization of the reconstituted YFP fluorophore with TMR fluorophore was seen at the plasma membrane only in 15 seconds after $PTH^{TMR}$ stimulation, and in intracellular puncta at 30 minutes (data not shown). Almost all the reconstituted YFP associated with $PTH^{TMR}$. The observation was further confirmed by the immunostaining of TβRII and PTH1R in the $PTH^{TMR}$-treated cells. TβRII, PTH1R, and PTH ligand predominantly colocalize into the same cytoplasmic vesicles (data not shown).

Figure 11:
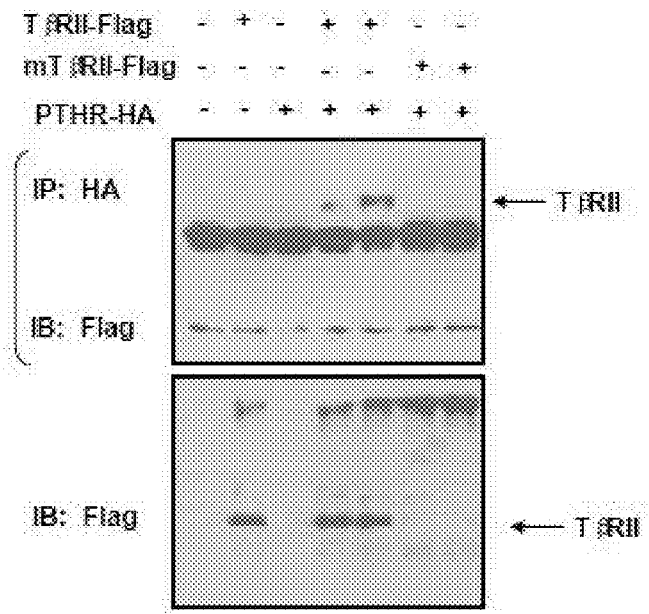
Figure 11:
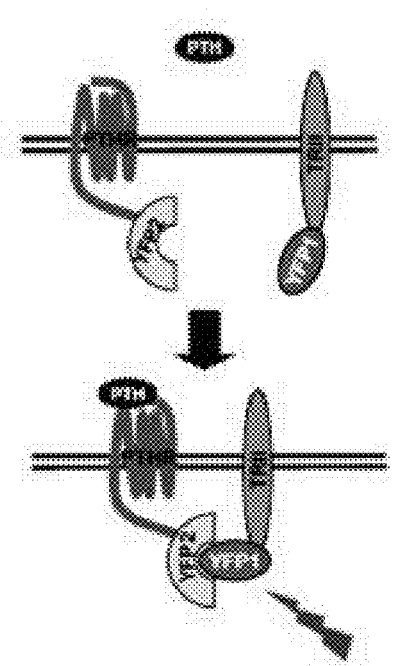

Next, the interaction was examined using a biochemical approach. PTH1R-HA was contransfected in HEK293 cells with Flag-TβRII. The cell lysate was subjected to HA immunoprecipitation, and associated TβRII was immunoblotted with anti-Flag antibody. TβRII specifically coprecipitated with PTH1R (FIG. 11) in 10% FBS medium, and the interaction was enhanced by PTH stimulation, whereas the kinase-dead mutant of TβRII lost the interaction with PTH1R (data not shown) even with treatment of PTH. The interaction of endogenous PTH1R and TβRII was also examined. TβRII was immunoprecipitated and PTH1R in the immunocomplex was immunoblotted. PTH induced the interaction (FIG. 11). Interestingly, the size of precipitated endogenous PTH1R was approximately 160 kDa, suggesting that endogenous PTH1R dimers interact with TβRII. Together, these results indicate that PTH induced interaction between PTH1R and TβRII, and recruits TβRII through PTH1R as an essential endocytotic component.

Example 11

PTH Induces Interaction of TGFβRII with PTH1R Dimer and Attenuates TGFβ/Smad Signaling To examine the effect of PTH on dimerization of PTH1R, PCA was performed with fusion of YFP1 and YFP2 fragments into cytoplasmic tail of PTH1R. Expression of PTH1R-YFP1 and PTH1R-YFP2 alone or both did not generate any fluorescence (FIG. 12A). Stimulation of PTH (1-34) rapidly reconstitutes YFP fluorescence on plasma membrane when both PTH1R-YFP1 and PTH1R-YFP2 were expressed. Importantly, TβRII immunostained with Flag antibody colocalized with the YFP fluorophore at plasma membrane and cointernalized into intracellular pucta in 30 minutes. The results, together with the previous observations, demonstrate that PTH induces the formation of PTH1R dimer/polymer and recruits TβRII to the PTH/PTH1R complex. Thus, PTH, PTH1R dimer/polymer, and TβRII formed a ligand/receptors complex to initiate the endocytosis.

Since β-arrestin has been shown to mediate GPCR internalization, the endocytotic pathway was examined for a PTH/PTH1R/TβRII complex. The binding of PTH on the cell surface activated β-arrestin-mediated endocytosis (data not shown). When cells were transfected with TβRII-Flag and PTH1R-HA, and immunostained with Flag and HA antibodies, TβRII coupled with PTH ligand and PTH1R, presenting in the β-arrestin-labeled cytoplasmic vesicles (data not shown). These results indicated that PTH-induced endocytosis of TβRII goes through the crathrin-mediated pathway.

It has been reported that TGFβ-induced endocytosis of TGFβ/TβRII is mediated by Sara endosome. The response of TβRII to PTH was analyzed to determine whether it is the same as to TGFβ. When Sara-Flag was overexpressed in the cells, it was observed as intracellular dots that colocalized with TβRII in response to TGFβ stimulation, but did not colocalize with TβRII/PTH1R complex induced by PTH. The result indicated that PTH acted through a distinct pathway with TGFβ to internalize TβRII and clear TβRII from the cell surface membrane. In TGFβ sensitive C2C12 cells, phosphorylation of Smad2 was activated by TGFβ stimulation, whereas when the cells were pretreated with PTH, phosphorylation of Smad2 by TGFβ was largely inhibited (FIG. 12A). The observation was confirmed by TGFβ-induced interaction between Smad2 and Smad4. Pretreatment with PTH inhibits the interaction (FIG. 12B). Finally, expression of PTH1R inhibits the activation of TGFβ to the Smad1-binding-element (SBE) luciferase report, and PTH enhanced the inhibition (FIG. 12C). Taken together, these results demonstrate that PTH-induced internalization of TβRII/PTH1R complex attenuates the TGFβ/Smad signaling by decreasing the cell membrane level of TβRII.

Example 12

TGFβRII Kinase-Dead Mutant Disrupts PTH1R-TGFbRII Interaction and Endocytosis

The potential role of the TβRII kinase activity in TβRII-mediated PTH endocytosis was examined. The YFP1 fragment was fused to the C-terminal of TβRII comprising a point mutation in the kinase domain (K277A), which has no kinase activity. The YFP2 fragment was fused to the C-terminal of PTH1R. Both WT TβRII-YFP1 and kinase dead TβRII (K227A)-YFP1 were co-expressed with PTH1R-YFP2, and the fluorescence produced through PTH1R-TβRII complementary interaction in living cells was measured (data not shown). The intensity of the fluorescence in cells expressing TβRII (K227A) was only one sixth of that in WT TβRII, suggesting the kinase activity is involved in the recruitment of TβRII to PTH1R (FIG. 13B). TβRII (K227A) significantly reduced internalization of PTH1R (FIG. 13A). This result also was demonstrated with immuno-colocalization, where PTH1R was primarily localized at the membrane in cells expressing TβRII (K227A), whereas PTH1R was internalized when WT TβRII was expressed (FIG. 13B). To confirm the observation, the PTH1R on membrane was measured for the cells transfected with WT TβRII, TβRII (K227A), or vector. PTH ligand was incubated with the transfected cells for 15 seconds. After washing, the plasma membrane was isolated, and the amount of PTH ligands bound to membrane PTH1R was measured by Western blot analysis. Overexpression of WT TβRII reduced binding of PTH ligands about 50% in the cell membrane in comparison with vector control, whereas kinase dead TβRII (K227A) showed an increase of ligand binding (FIG. 13C), suggesting that the membrane PTH1R is internalized with expression of WT TβRII, and that the kinase activity of TβRII is required for the process. Furthermore, TβRII (K227A) did not reduce PTH-induced phosphorylation of PTH1R (FIGS. 13D and 13E)

Example 13

TGFβRII Inhibits PTH-Induced Activation of cAMP by Decreasing Membrane PTH1R

FIG. 14 demonstrates that TGFβRII inhibits PTH-induced activation of cAMP by decreasing membrane PTH1R. TGFβRII inhibits PTH-induced activation of CREB responsive luciferase activity (Panel A). TGFβRII inhibits PTH-induced phoshorylation of CREB (Panel B). TGFβRII inhibits PTH-induced camp (Panel D). TGFβRII inhibits PTH-induced IP3 activity, and TGFβRII enhances internalization of TMR labeled PTH ligand.

Example 14

PTH Induces PTH1R Interaction with Both BMPRII Long Form and Short Form

Embryonic kidney 293 cells were transfected with HA-PTH1R and myc-BMPRII long form (FIGS. 15A, 15B, and 15C), or Flag-BMPRII short form (FIGS. 15A and 15B) with Lipofectamine Plus reagent (Invitrogen, Cat. No. 10964-013). The PTH1R, BMPRII short form, and BMPRII long form sequences were all of human origin and were carried on pcDNA vectors (Invitrogen). The transfected cells were treated with vehicle or PTH (1-34) (BioChem. Inc.) for 24 hours (FIG. 15C). The cells were cultured in DMEM with 10% serum and were split at 30%-40% confluent.

Immunoprecipitation assays were performed as described previously (Shi et al., 2004, J. Cell. Biol. 164:291-300). BMPRII was immunoprecipitated from the cell extracts using anti-Myc (Sigma C-3956; 1:200-500 dilution) or anti-Flag M2 antibodies (Sigma F-3165; 1:1000 dilution), and the immunocomplex was detected by Western blotting with HA antibody (CVANCE MMS-101; 1:1000 dilution) specific for PTH1R. Alternatively, PTH1R was immunoprecipitated first using anti-HA antibody, and the immunocomplex was detected by Western blotting with anti-Myc and anti-Flag antibodies specific for the BMPRII long and short forms. The results demonstrated that both long and short forms of BMPRII interact with PTH1R (FIGS. 15A and 15B) and that PTH induces the interaction (FIG. 15C).

Example 15

PTH Induces Endogenous PTH1R Interaction with ActRII and ActRIIB

Embryonic kidney 293 cells in DMEM with 10% serum were treated with vehicle (water) or PTH (1-34) (50 nM). The cells were cultured in DMEM with 10% serum and were split at 30%-40% confluent.

Immunoprecipitation assays were performed as described previously (Shi et al., 2004, J. Cell. Biol. 164:291-300). ActRII and ActRIIB were immunoprecipitated from the cell extracts using anti-ActRII or ActRIIB antibodies (R & D Systems, Inc.; 1:200-500 dilution), and the immunocomplex was detected by Western blotting with an antibody specific for PTH1R (Santa Cruz Biotechnology, Inc.; 1:200-500 dilution) to detect PTH1R protein. The results indicate that both ActRII and ActRIIB interact with PTH1R, and PTH enhances the interaction.

Example 16

BMPRII Regulates PTH-Induced PKA and PKC Activity 293 cells were transfected with BMPRII long form, short form, and dominant negative expression plasmids (all pcDNA3 vectors) using Lipofectamine Plus reagent (Invitrogen, Cat. No. 10964-013). The cells were cultured in DMEM with 10% serum and were split at 30%-40% confluent.

The transfected cells were treated with vehicle or PTH (1-34) (50 nM) in DMEM with 10% serum. The transfected cells were harvested and lysed. PKA (FIG. 17A) and PKC (FIG. 17B) activities were measured using the PepTag Assay for Non-radioactive Detection of Protein Kinase C or cAMP Dependent Protein Kinase (Promega) according to the manufacturer's instructions. The results of these assays, shown in FIG. 17 as a relative fold change, indicate that BMPRII long form and short form regulate PTH-induced PKA and PKC activity.

Example 17

ActRIIA and ActRIIB Enhance Binding of PTH to its Receptors

FIG. 18 is a photomicrograph demonstrating that ActRIIA and ActRIIB enhance binding of PTH (1-34) to its receptors. 293 cells were transfected with ActRIIA, ActRIIB, BAMBI, PTH1R expression plasmids, or with empty vector (all pcDNA3 vectors) using Lipofectamine Plus reagent (Invitrogen). The transfected cells were photo-labeled with $^{125}$I-PTH (1-34) (50,000 cpm/ml; labeled at the UAB Cancer Center). The cell lysates were analyzed on PAGE and exposed on film for 5 days.

We claim:

1. A method of identifying a compound, a parathyroid hormone (PTH) ligand, or a fragment of a PTH ligand that improves bone mass, comprising:
   a) contacting an in vitro cell expressing a PTH receptor with a test compound, a PTH ligand, or a fragment of a PTH ligand, wherein the PTH receptor is selected from the group consisting of low density lipoprotein related protein (LRP) 5/6, transforming growth factor beta receptor, type II (TGFβRII), bone morphogenic protein receptor, type II (BMPRII), activin A receptor, type IIA (ActRII), and activin A receptor, type IIB (ActRIIB); and
   b) determining whether an increase in binding between the PTH receptor and parathyroid hormone 1 receptor (PTH1R) occurs in the cell contacted with the compound, the PTH ligand, or the fragment of a PTH ligand, as compared to a control, said increase being an indication that the compound, PTH ligand, or fragment of PTH ligand improves bone mass.

2. The method of claim 1, wherein the PTH receptor is LRP5/6.

3. The method of claim 1, wherein the PTH receptor is TGFβRII.

4. The method of claim 1, wherein the PTH receptor is BMPRII short form, BMPRII long form, ActRII, or ActRIIB.

5. A method of identifying a compound, a parathyroid hormone (PTH) ligand, or a fragment of a PTH ligand that enhances the interaction of parathyroid hormone 1 receptor (PTH1R) with a PTH receptor, comprising:
   a) contacting an in vitro cell expressing a PTH receptor with a test compound, a PTH ligand, or a fragment of a PTH ligand, wherein the PTH receptor is selected from the group consisting of transforming growth factor beta receptor, type II (TGFβRII), bone morphogenic protein receptor, type II (BMPRII), activin A receptor, type IIA (ActRII), activin A receptor, type IIB (ActRIIB), and low density lipoprotein related protein (LRP) 5/6; and
   b) determining whether binding of PTH1R with the PTH receptor is increased in the presence of the test compound, the PTH ligand, or the fragment of a PTH ligand, as compared to a control, an increase in said binding being an indication that the test compound, the PTH ligand, or the fragment of a PTH ligand enhances the interaction of PTH1R with the PTH receptor.

6. The method of claim 5, wherein the PTH receptor is LRP5/6.

7. The method of claim 5, wherein the PTH receptor is TGFβRII.

8. The method of claim 5, wherein the PTH receptor is BMPRII short form, BMPRII long form, ActRII, or ActRIIB.

* * * * *